United States Patent
Kondou et al.

(10) Patent No.: US 10,622,093 B2
(45) Date of Patent: Apr. 14, 2020

(54) METHOD AND DEVICE FOR CORRECTING LEVEL OF EXPRESSION OF SMALL RNA

(71) Applicant: Toray Industries, Inc., Tokyo (JP)

(72) Inventors: Satoshi Kondou, Kamakura (JP); Satoko Kozono, Kamakura (JP)

(73) Assignee: Toray Industries, Inc., Tokyo (JP)

( * ) Notice: Subject to any disclaimer, the term of this patent is extended or adjusted under 35 U.S.C. 154(b) by 0 days.

(21) Appl. No.: 15/529,165

(22) PCT Filed: Nov. 25, 2015

(86) PCT No.: PCT/JP2015/083079
§ 371 (c)(1),
(2) Date: May 24, 2017

(87) PCT Pub. No.: WO2016/084848
PCT Pub. Date: Jun. 2, 2016

(65) Prior Publication Data
US 2017/0351809 A1 Dec. 7, 2017

(30) Foreign Application Priority Data
Nov. 26, 2014 (JP) .................. 2014-238451

(51) Int. Cl.
*C12Q 1/68* (2018.01)
*G16B 25/00* (2019.01)
(Continued)

(52) U.S. Cl.
CPC .............. *G16B 25/00* (2019.02); *C12M 1/00* (2013.01); *C12N 15/09* (2013.01); *C12Q 1/68* (2013.01);
(Continued)

(58) Field of Classification Search
None
See application file for complete search history.

(56) References Cited

U.S. PATENT DOCUMENTS

2010/0184608 A1   7/2010 Russwurm et al.

FOREIGN PATENT DOCUMENTS

JP   2007-75095 A   3/2007
JP   2007-97429 A   4/2007
(Continued)

OTHER PUBLICATIONS

Mestdagh et al. (Genome Biology, 2009, 10(6):R641-10) (Year: 2009).*
Sarkar et al. (Nucleic Acids Research, 2009, 37(2):e37, p. 1-8) (Year: 2009).*
Van Vlierberghe et al. (Blood, 2006, 108(10):3520-3529) (Year: 2006).*
(Continued)

*Primary Examiner* — Stephanie K Mummert
(74) *Attorney, Agent, or Firm* — DLA Piper LLP (US)

(57) ABSTRACT

A method of correcting an expression level(s) of a target small RNA(s) for comparative analysis of the expression level(s) in a plurality of samples includes adding at least one kind of standard substance to each of the plurality of samples, extracting nucleic acids from each sample to obtain a nucleic acid sample; measuring the amounts of the target small RNA(s) and the standard substance(s) present in each extracted nucleic acid sample; obtaining a representative value from the measured value(s) of the amount(s) of the standard substance(s) extracted; obtaining the difference or the ratio between a reference value arbitrarily set in connection with the amount(s) of the standard substance(s) extracted and the representative value of the standard substance(s) obtained for each sample; and correcting the expression level(s) of the target small RNA(s).

11 Claims, 4 Drawing Sheets

Specification includes a Sequence Listing.

Distributions of measured values of small RNAs

Distributions of measured values of small RNAs

Representative values of measured values of standard substances

Representative values of measured values of standard substances

(51) Int. Cl.
 C12M 1/00 (2006.01)
 C12N 15/09 (2006.01)
 C12Q 1/6883 (2018.01)
(52) U.S. Cl.
 CPC ..... *C12Q 1/6883* (2013.01); *C12Q 2600/158* (2013.01); *C12Q 2600/178* (2013.01)

(56) References Cited

FOREIGN PATENT DOCUMENTS

| JP | 2010-519893 A | 6/2010 |
| JP | 2011-239708 | 12/2011 |
| JP | 5229895 B2 | 7/2013 |
| JP | 2014-7995 A | 1/2014 |
| WO | 2011/057003 A2 | 5/2011 |
| WO | 2011/145614 A1 | 11/2011 |
| WO | 2013/020058 A1 | 2/2013 |

OTHER PUBLICATIONS

Sarkar et al. (Nucleic Acids Research, 2009, 37(2):e17, p. 1-8) (Year: 2009).*
Kosaka, N., *Circulating MicroRNAs: Methods and Protocols( Methods in Molecular Biology)*, Humana Press, New York, 2013, p. 1-10.
Anonymous: "GeneChip? miRNA Array", Jan. 1, 2009, Retrieved from the Internet: URL:http://media.affymetrix.com/support/technical/datasheets/mRNA.datasheet.pdf. 2 pages.
N. Fahlgren et al , "Computational and analytical framework for small RNA profiling by high-througput sequencing", *RNA*, vol. 15, No. 5, Mar. 24, 2009, pp. 992-1002.
Thomas C. Roberts et al.: "Assessment of RT-qPCR Normalization Strategies for Accurate Quantification of Extracellular microRNAs in Murine Serum" *PLOS ONE*, vol. 9, No. 2, Feb. 19, 2014, e89237-1, 9 pages.
The Extended European Search Report dated May 16, 2018, of counterpart European Application No. 15863331.3.

* cited by examiner

SEQUENCE LISTING

```
<160> NUMBER OF SEQ ID NOS: 17

<210> SEQ ID NO 1
<211> LENGTH: 533
<212> TYPE: RNA
<213> ORGANISM: Artificial Sequence
<220> FEATURE:
<223> OTHER INFORMATION: designed sequence

<400> SEQUENCE: 1
gggcucgacu aguuaauacg guacaggaua accgaucggc uugcaacaua acggcguuaa    60
gaaugcggga gugcaguuuc cgauucucac aucaaucgcc aauaaggccu ugucgcaaua   120
uagacucaac gguucuagua gcugaucggu auuacgugac gcaaccgauu agacaugcac   180
aauuccuugg ucgcuauacu acggaaaucg ucagguacua uaacccgucg caggccuaau   240 acgucguc acaucgccaa ccuaucguca gucggaaaga cguugcuguc uaccaucgaa    300
acuauuuacc gcuccgagau ucacgaguac gaacucacga ggaaguugcc cuauguaagg   360
```

| | |
|---|---|
| uaucacuccca gguacugcgc cgauaguacc aggugaucaa acgguugcaa aaggccacg | 420 |
| acguaucggg cucuuuagac guacgcucga gauuaaacgc gcacugauuc acuuuagccc | 480 |
| ggaaugucuc ggugcgaugu agaaaaaaaa aaaaaaaaaa aaaaaaaaaa aaa | 533 |

<210> SEQ ID NO 2
<211> LENGTH: 533
<212> TYPE: RNA
<213> ORGANISM: Artificial Sequence
<220> FEATURE:
<223> OTHER INFORMATION: designed sequence

<400> SEQUENCE: 2

| | |
|---|---|
| gggagacuaa aucucggcgu cgguucauac gcgcgaucgu uugcugucag ggcauacucg | 60 |
| aauccggacu ccgacaauua uaggccaucc ugaauagccg aucaugcgag ucacgauaag | 120 |
| gcaggcucug cgauaucccg auauacugga gaagcugaau cccaccuaga gcgaacuguc | 180 |
| agaggaucga ccucaggcuc gcaucauca uaacggcgga cgaccugugu cacauuccga | 240 |
| acgcuacgug acgauauuau cugucgaaag gcauagaacg ccggucaaua uccugcggca | 300 |
| uucucuuuau caccggcuau aacuacuagg uuccgcagau auagacugcg cacggaacau | 360 |
| guagauagau cgaguagggu agcgauuuaa cgacucgacu uacagacaga gacguagaac | 420 |
| gucagacgag ugguaugccc accagaggcg auacaggcug uaccgcgua gcacuagagu | 480 |
| cgugcgucau gcggacccua ucuaaaaaaa aaaaaaaaaa aaaaaaaaaa aaa | 533 |

<210> SEQ ID NO 3
<211> LENGTH: 533
<212> TYPE: RNA
<213> ORGANISM: Artificial Sequence
<220> FEATURE:
<223> OTHER INFORMATION: designed sequence

<400> SEQUENCE: 3

| | |
|---|---|
| gggacuaaac gcacugaaua ccguacuaca acagacgaag uuguaaauag ccgugguaau | 60 |
| uaugaacgaa uauggccaug uguccgcuaa uccgcgguac uagccaguua gcaacugcac | 120 |
| caaucgcuca cgucagguggu ucuaugcaau augcuccagu acccuguaag uucgcaauca | 180 |
| auagacgcgc cuuacuccuc ucaagaaggg uaucugcaug agccgacaca ucaagaccca | 240 |
| auggacguuu gagcgagugg cuggagagu auuaacgcac uaacucuucg aaggcuuacu | 300 |
| ucggcaaauc cgcgagcucc acuauuaaca ugccaauacg acaggaucaa uucugcgacu | 360 |
| gcacgaccga auuaugcacc uacuuuguga ggcacgagau cgucuugca gcuauuuaaa | 420 |
| ggguuccagc uuauggauag gcgacucuuc agugcguaau aaagcaacgc ccaaucggca | 480 |
| uguuaccgga uaguacgggc gauaaaaaaa aaaaaaaaaa aaaaaaaaaa aaa | 533 |

<210> SEQ ID NO 4
<211> LENGTH: 1033
<212> TYPE: RNA
<213> ORGANISM: Artificial Sequence
<220> FEATURE:
<223> OTHER INFORMATION: designed sequence

<400> SEQUENCE: 4

| | |
|---|---|
| gggcgauucg aagagguacg aguggacgcg uaagcgaaug accuagaccu cggcguuaau | 60 |
| uaggacccuc uaaucgcaaa cucgacucuc guccccaaucc aauggaugcu cagugcucgg | 120 |
| uagcaugauc guaugaugcg uaucgcugcg aguagaggcc gacaaguaga ccggugcgaa | 180 |

| | |
|---|---|
| uuuggaggua cuuagccuca uaugagagcg ccugaaauc acccagugcc gaucguagcg | 240 |
| gaagauuacu agacuccgca gggaaauccc accuguaacg acggaagagc gucacgauag | 300 |
| ccucuaacua uccgguucgc gacuauccgc uuaugugccu ccaccuaaug ugagaguuca | 360 |
| ccgaggcaaa ugaucuguca accggugugu caggacaua cgcuuaaugc cguagaagcc | 420 |
| cguaagcucu ccgcccuuua agagguugua gacggcaguu cuaaggucgu cggggucuaug | 480 |
| ccuugcgacc uaauaauacg accgugugcu uaugcggacu guccucuaau gaauaucgcu | 540 |
| uguccuaagc uggcgguacu agugcuuagg aucgcacacc ucaccacagu gcgcauuuaa | 600 |
| cccuguagau aacaugguag acaccgguaa aucgcguucg aauucgcccc aaucgaaggc | 660 |
| ccacaucacu acgucgccug uauucugaac cuugcgcugc acguagcaua uagagcguac | 720 |
| auucaaucua ccaguugccu ccgacugaag ucggcuagcg uaugacauag cgagcucuua | 780 |
| guucggugac uacuucuagc acucccaauu caagcucugc guuaucaggg ucggaagguu | 840 |
| agguucgaau uucgacaggc uaacagagcg auaagugaug aauccgcucc gggagcaucu | 900 |
| agacaauaac cgcgguuaag agaagggcga cauaagcgcg ggugucaacg uucaaaccag | 960 |
| uuguagccau cgcgauuacc cguugggaau cugaggcgac cuaaaaaaaa aaaaaaaaaa | 1020 |
| aaaaaaaaaa aaa | 1033 |

<210> SEQ ID NO 5
<211> LENGTH: 1033
<212> TYPE: RNA
<213> ORGANISM: Artificial Sequence
<220> FEATURE:
<223> OTHER INFORMATION: designed sequence

<400> SEQUENCE: 5

| | |
|---|---|
| gggauuccua ggacuguacu cucggugcgu ugaccauacg uaaggcgauc cuuugagugg | 60 |
| aucccauuac uacgcgucac accugcuuac ccucccaaua guugguucag uagcucucag | 120 |
| cgguucuggc agaguucgga ugaguuucug ccaucaguu cauaggugcc cacgcauugg | 180 |
| guccacuccu cgccagaauu ugcgcauugc accauuacua caggcggcuu ugguuguacg | 240 |
| ucuaacguuc gcaccaacag gagucucagc ugaucauagg cccggacccu caauguucga | 300 |
| ugcgauucgu aagagggugu ucguguaagg cccaauacgu ugucaugccg gcuuagaaac | 360 |
| ccagucggac gcgucucuaa cacucggaug ugcagguaau agccuuuacc agcgcuucug | 420 |
| uacgaccaua cuuagagcuc gagaugccga caugaaagga uuccggagua cugaccugaa | 480 |
| uacacguuca uagcguaaau cggccgagau ucaacuuuac ggcacggaua cagcccucu | 540 |
| accuauuucc gucgaagucu cucacgauag ucgcguacau uuaguggcg guacacacag | 600 |
| cacgucaacg ccaucgcacu cugaguuccc acuccacggu acguuacag cacguugccu | 660 |
| uaauaagcua cuucgguucc gagcagucaa ccuacuguuu ccggguuagc gcucugauca | 720 |
| gcacccguuu acugacacga accgcuaucg aauacgagu aggucgugug ccaauaacuu | 780 |
| ugguugcagc uaagcuaauc ggacggcgac uuuagcaagu aacucagccg uauuguuacg | 840 |
| cugaccguaa acgacgugag cgauugucgu agguuagcca uaacauaaag guuucccgaa | 900 |
| cgguagcaua guuaggccug ugccagucag gguaauacga gaguaauu aacgcgaucu | 960 |
| aaugagaagc cgugcauguc gauccuuguu acggguguga aauaaaaaaa aaaaaaaaaa | 1020 |
| aaaaaaaaaa aaa | 1033 |

<210> SEQ ID NO 6
<211> LENGTH: 22

```
<212> TYPE: RNA
<213> ORGANISM: Caenorhabditis elegans

<400> SEQUENCE: 6
ucaccgggug uaaaucagcu ug                                              22

<210> SEQ ID NO 7
<211> LENGTH: 24
<212> TYPE: RNA
<213> ORGANISM: Caenorhabditis elegans

<400> SEQUENCE: 7
uacccguaau cuucauaauc cgag                                            24

<210> SEQ ID NO 8
<211> LENGTH: 21
<212> TYPE: RNA
<213> ORGANISM: Arabidopsis thaliana

<400> SEQUENCE: 8
uuuggauuga agggagcucu a                                               21

<210> SEQ ID NO 9
<211> LENGTH: 23
<212> TYPE: RNA
<213> ORGANISM: Caenorhabditis elegans

<400> SEQUENCE: 9
uuuguacucc gaugccauuc aga                                             23

<210> SEQ ID NO 10
<211> LENGTH: 69
<212> TYPE: RNA
<213> ORGANISM: Artificial Sequence
<220> FEATURE:
<223> OTHER INFORMATION: designed sequence

<400> SEQUENCE: 10
aacauaccgg ccucguccgu gcauuaaggu gggaacgaug auaaaggagc ucgauccauc      60
gcaugugac                                                             69

<210> SEQ ID NO 11
<211> LENGTH: 69
<212> TYPE: RNA
<213> ORGANISM: Artificial Sequence
<220> FEATURE:
<223> OTHER INFORMATION: designed sequnece

<400> SEQUENCE: 11
gcauuugcga uacaaacgga acuuauuagu agcuaaguca agguucuagc guucgucccg      60
aucgaauga                                                             69

<210> SEQ ID NO 12
<211> LENGTH: 69
<212> TYPE: RNA
<213> ORGANISM: Artificial Sequence
<220> FEATURE:
<223> OTHER INFORMATION: designed sequence

<400> SEQUENCE: 12
ccgaguucag cgauaaccgu gaccaguaac gguacccuag cgcauagcgc ggauguccga      60
gucaagaaa                                                             69
```

<210> SEQ ID NO 13
<211> LENGTH: 69
<212> TYPE: RNA
<213> ORGANISM: Artificial Sequence
<220> FEATURE:
<223> OTHER INFORMATION: designed sequence

<400> SEQUENCE: 13
gucuugcaua uacccaccgc auguugcucg ucgcgacaua aacgacgaua ccucauauag    60
cacuuaguu                                                           69

<210> SEQ ID NO 14
<211> LENGTH: 69
<212> TYPE: RNA
<213> ORGANISM: Artificial Sequence
<220> FEATURE:
<223> OTHER INFORMATION: designed sequence

<400> SEQUENCE: 14
aggucagauu cuuauuagaa cguguguccg cuccgaccau agggcgcccg uuacucagac    60
gcguuugug                                                           69

<210> SEQ ID NO 15
<211> LENGTH: 201
<212> TYPE: RNA
<213> ORGANISM: Artificial Sequence
<220> FEATURE:
<223> OTHER INFORMATION: designed sequence

<400> SEQUENCE: 15
aaccggccga auaguacgug auaaccggcc gaauaguacg ugauaaccgg ccgaauagua    60
cgugaucucg cuaguaggua cggcuucacu cgcuaguagg uacggcuuca cucgcuagua   120
gguacggcuu cacuuucuag cuaaacgccu cguugcuuuc uagcuaaacg ccucguugcu   180
uucuagcuaa acgccucguu g                                            201

<210> SEQ ID NO 16
<211> LENGTH: 200
<212> TYPE: RNA
<213> ORGANISM: Artificial Sequence
<220> FEATURE:
<223> OTHER INFORMATION: designed sequence

<400> SEQUENCE: 16
uucgacgggu aucguuuuag gcuccgacgg guaucguuuu aggcuccgac ggguaucguu    60
uuaggcucgc cgcuauugu cgcguaauug cccgcuauug ucgcguaauu gcccgcuauu   120
gucgcguaau ugcgcaugcg uaguaaccuc ugaagugcau gcguaguaac cucugaagug   180
caugcguagu aaccucugaa                                              200

<210> SEQ ID NO 17
<211> LENGTH: 204
<212> TYPE: RNA
<213> ORGANISM: Artificial Sequence
<220> FEATURE:
<223> OTHER INFORMATION: designed sequence

```
<400> SEQUENCE: 17
ggauugcaau cucgaguacc guuggauugc aaucucgagu accguuggau ugcaaucucg          60
aguaccguuc ucagcgaaau uuucggcguu acucagcgaa auuuucggcg uuacucagcg         120
aaauuuucgg cguuagcauu cccacgccau accuuuaugc auuccacgc cauaccuuua          180 ugcauuccca cgccauaccu uuau                                                 204
```

METHOD AND DEVICE FOR CORRECTING LEVEL OF EXPRESSION OF SMALL RNA

TECHNICAL FIELD

This disclosure relates to a method of correcting an expression level(s) for comparative analysis of the expression level(s) of a target small miRNA(s) contained in a plurality of samples, and a device that corrects the expression level(s).

BACKGROUND

Non-coding RNA (ncRNA) is a general term for RNAs that do not encode protein, and roughly divided into house-keeping RNAs and regulatory RNAs. There are ncRNAs having various lengths, and ncRNA molecules with less than 200 bases are called small RNAs.

Known examples of house-keeping RNAs include ribosomal RNA (rRNA); transfer RNA (tRNA); small nuclear RNA (snRNA), which is involved in splicing; and small nucleolar RNA (snoRNA), which is involved in modification of rRNA.

In recent years, regulatory RNAs have been attracting attention as factors having important functions for elucidation of biological functions. It is recently becoming clear that regulatory RNAs regulate gene expression and intracellular distribution of RNAs to play important roles in a gene expression-suppressing mechanism. The gene expression-suppressing mechanism in which regulatory RNAs function is called RNA interference (RNAi). This mechanism was revealed by experiments using *C. elegans* in 1988, and the presence of similar mechanisms in *Drosophila* and mammalian cells was revealed thereafter. ncRNAs as the regulatory RNAs have a chain length of about 20 to 25 bases, and their action mechanisms can be roughly divided into translational repression by microRNA (miRNA) and gene silencing through cleavage of a target mRNA by small interference RNA (siRNA) and heterochromatinization of a target DNA region.

A miRNA is transcribed as an RNA (precursor) having a hairpin-like structure from genomic DNA. This precursor is cleaved by a particular enzyme, dsRNA cleavage enzyme (Drosha, Dicer) having RNase III cleavage activity, and converted into a double-stranded form and then into single strands. It is thought that the antisense strand, which is one of the double-strands, is incorporated into a protein complex called RISC and the RISC are involved in suppression of translation of mRNA. Thus, miRNA takes various forms in the various stages after its transcription. Therefore, when targeting (detecting) a miRNA, various forms including the hairpin structure, double-stranded structure, and single-stranded structure need to be taken into account. A miRNA is an RNA of 15 to 25 bases, and the presence of miRNAs has been confirmed in various organisms.

In recent years, it has been suggested that a large amount of miRNAs are present in not only cells, but also body fluids such as serum, plasma, urine, and spinal fluid, which are samples (biological samples) containing no cells, and that the expression levels of those miRNAs should become biomarkers for various diseases including cancers. As of June 2014, there were no less than 2500 kinds of miRNAs in human (miRBase release 20) and, when a gene expression assay system such as a highly sensitive DNA microarray is used, expression of more than 1000 kinds of miRNAs among them can be detected simultaneously in serum or plasma. Thus, many studies are being carried out to find biomarkers by DNA microarray in body fluids such as serum/plasma, urine, and spinal fluid.

On the other hand, it is well known that, when gene expression analysis is carried out using a DNA microarray, the obtained data will include some errors depending on the sample, experimenter, and experimental conditions. Thus, methods of correcting measured values including such errors have been examined. Methods often used for the correction of the data are based on the principle that, when measured values of the expression levels of a plurality of genes are treated as a single cluster to be regarded as a gene expression data group, there is no difference in the expression level among any samples. Examples of such methods include the global normalization method, quantile method, lowess method, and 75 percentile method. However, these correction methods have the drawback that they can be used only when comprehensive detection of more than a certain number of genes is carried out.

On the other hand, there are also methods in which particular genes (for example, beta-actin and GAPDH) whose expression levels are the same among samples are used to correct data from each sample such that the measured values of such particular genes become constant value.

Also, when small RNAs are analyzed with a DNA microarray, a correction method used for gene expression analysis such as the global normalization method, quantile method, lowess method, or 75 percentile method described above is used. However, those methods cannot be used when only a particular gene(s) is/are to be detected. On the other hand, as methods of performing the correction such that the expression levels of particular genes become constant expression value, methods in which, among the small RNAs expressed in samples, housekeeping RNAs (U1 snoRNA, U2 snoRNA, U3 snoRNA, U4 snoRNA, U5 snoRNA, U6 snoRNA, 5S rRNA, and 5.8S rRNA) are used for the correction have been proposed (JP 2007-75095 A and JP 2007-97429 A).

In JP 2007-75095 A and JP 2007-97429 A, in detection of a miRNA which is a small RNA, the miRNA detection results are corrected such that the detection value of 5S rRNA detected simultaneously becomes constant value across all samples. However, there is no guarantee that the expression level of 5S rRNA is constant among the samples.

In JP 2014-007995 A, in detection of a miRNA which is a small RNA, mRNAs are detected simultaneously, and their representative value is used to correct the miRNA detection results. That method is also applicable when more than a certain number of mRNAs are detected and the distribution of the values of detected mRNAs is secured as the normal distribution.

Thus, for correction of errors in the expression levels among experiments, methods in which a nucleic acid standard substance is used in the process of the experiments, and the detected abundances of the standard substance are used to correct the errors among the experiments have been proposed (JP 2011-239708 A, JP 5229895 B and US 2010/0184608 A). JP 2011-239708 A and JP 5229895 B propose the sequence of the nucleic acid standard substance, the sequence of the nucleic acid probe for detection of the standard substance, and how to design them, and show the accuracy in the amplification step and the detection step so that evaluation of the performances of the detection methods is possible therewith. However, those publications do not actually show correction of errors among experiments including the step of extraction of nucleic acid from samples. US 2010/0184608 A also shows the sequence of a nucleic acid standard substance for correction of errors in the detection values of gene expression in samples. However, since that sequence is used in the step after amplification of nucleic acid, it merely allows correction of errors in the amplification step among experiments.

That is, the methods shown in JP 2011-239708 A, JP 5229895 B and US 2010/0184608 A enable evaluation of the accuracy and correction of errors in the measurement step including amplification and detection of nucleic acid only when a sufficient amount of nucleic acid is extracted from the samples, and the nucleic acid used can be quantified with high accuracy. However, when correction of measurement results is actually carried out among experiments, especially when small amounts of samples are used or when a body fluid is used as the samples, the amount of the target small RNA extracted is very small, and high accuracy measurement is impossible because of small amount of small RNA. Thus, correction by such methods is substantially impossible. It is therefore very important to carry out correction of errors among experiments including not only the step of detection of a small RNA, but also the step of its extraction from samples.

In view of the above, as methods of evaluating/correcting errors among experiments including the step of extraction from samples, methods using a standard substance have been studied. To date, correction using a standard substance that is a nucleic acid having a base length similar to those of small RNAs has been studied. For example, methods in which a short RNA having a base length of about 20 bases, which is a base length similar to those of miRNAs, as shown in Nobuyoshi Kosaka Edit., "Circulating MicroRNAs: Methods and Protocols (Methods in Molecular Biology)", p 1-p 10, Human Press, New York (2013), is used as a standard substance, and extraction is carried out after adding a predetermined amount of this short RNA to samples, to carry out correction of errors in the step of extraction of a target small RNA in each experiment have been proposed.

For comparative analysis of the expression levels of target small RNAs among samples, correction of errors in the experimental conditions among the samples, especially correction of the difference in the extraction efficiency in the step of extraction of nucleic acid from the samples, is necessary. Although global normalization and normalization methods using house-keeping RNAs have been commonly used so far, they have drawbacks in targeting small RNAs as described above such as requirement of comprehensive detection of a large number of small RNAs and the absence of house-keeping RNAs whose constant expression can be secured among samples. Thus, those methods cannot be said to be effective for comparative analysis.

As described above, for the correction methods using a standard substance, correction using a nucleic acid standard substance having a base length similar to those of the target small RNAs has been studied. However, when an RNA having a base length similar to those of the target small RNAs is actually used as a standard substance, especially when a body fluid is used as the samples, the efficiency of extraction of the standard substance from the samples is unstable due to the influence of various conditions of the samples and various impurities contained therein, which results in instability of the measured values, and thus the accuracy cannot be secured. Therefore, the methods could not be used to correct measurement results among experiments.

Thus, to date, there has been no effective correction method utilizing a standard substance for comparative analysis of the expression levels of target small RNAs extracted from each sample, which method allows accurate correction of the measured values of the expression levels among the samples.

The Applicant hereby incorporates by reference the sequence listing contained in the ASCII text file titled SequenceListing.txt, created May 18, 2017 and having 8.60 KB of data.

SUMMARY

We discovered that, in a method of correcting the expression level(s) for comparative analysis of the expression level(s) of a target small RNA(s) contained in a plurality of samples, correction of the expression level(s) among the samples can be carried out more accurately than conventional methods by adding a standard substance(s) each of which is a nucleic acid having a nucleic acid length of not less than 200 bases, which is much longer than the small RNAs, to a predetermined amount of each of the plurality of samples, extracting nucleic acids from each sample, measuring the expression level of each target small RNA as well as the abundance(s) of the standard substance(s), and then carrying out correction using the measured value(s) of the abundance(s) of the standard substance(s).

We thus provide:

(1) A method of correcting an expression level(s) of a target small RNA(s) for comparative analysis of the expression level(s) in a plurality of samples, said method comprising:

an extraction step of adding at least one kind of standard substance to each of said plurality of samples, said standard substance being a nucleic acid with a nucleic acid length of not less than 200 bases, and then extracting nucleic acids from each sample to obtain a nucleic acid sample;

a measurement step of measuring the amounts of the target small RNA(s) and the standard substance(s) present in each extracted nucleic acid sample, to obtain measured values of the expression level(s) of the target small RNA(s) in, and the amount(s) of the standard substance(s) extracted from, each of the samples;

a representative-value-obtaining step of obtaining, for each of the samples, a representative value from the measured value(s) of the amount(s) of the standard substance(s) extracted;

a correction-factor-obtaining step of obtaining, as a correction factor for each sample for correction of the expression level(s) of the target small RNA(s) in said each sample, the difference or the ratio between a reference value that is arbitrarily set in connection with the amount(s) of the standard substance(s) extracted and the representative value of the standard substance(s) obtained for said each sample in the representative-value-obtaining step; and a correction step of correcting the expression level(s) of the target small RNA(s) measured in each sample using the correction factor obtained for said each sample.

(2) The correction method according to (1), wherein the nucleic acid length of said standard substance is 200 bases to 1200 bases.

(3) The correction method according to (2), wherein the at least one kind of standard substance includes at least one selected from standard substances that are nucleic acids whose base sequences are SEQ ID Nos:1 to 5 and 15 to 17.

(4) The correction method according to any one of (1) to (3), wherein two or more kinds of standard substances are used.

(5) The correction method according to any one of (1) to (4), wherein the sample is a sample derived from a body fluid.

(6) The correction method according to any one of (1) to (5), wherein the target small RNA is miRNA.

(7) The correction method according to any one of (1) to (6), wherein the extraction of the nucleic acid sample in said extraction step is carried out by the phenol-chloroform method.

(8) The correction method according to any one of (1) to (7), wherein said measurement step comprises carrying out hybridization by bringing a nucleic acid sample labeled with a labeling substance into contact with probes for capturing a plurality of target small RNAs and a probe(s) for capturing at least one standard substance, said probes being immobilized on a support, and obtaining the expression levels of the target small RNAs and the amount(s) of the standard substance(s) extracted, as signal intensity measurement values.

(9) The correction method according to any one of (1) to (8), wherein the representative value obtained in said representative-value-obtaining step is an average or a median expressed as a logarithmic value calculated from the measured value(s) of the amount(s) of the at least one standard substance extracted.

(10) The correction method according to any one of (1) to (9), wherein said reference value is a fixed value arbitrarily defined in connection with the amount(s) of the standard substance(s) extracted, or a representative value of the amount(s) of the standard substance(s) extracted obtained for a first sample arbitrarily selected from said plurality of samples.

(11) The method according to any one of (1) to (10), wherein the correction is carried out in said correction step as follows:

(a) when a value calculated by subtracting said reference value from said representative value is obtained as a correction factor in said correction-factor-obtaining step, the correction factor is subtracted from the measured value(s) of the expression level(s) of the target small RNA(s);

(b) when a value calculated by subtracting said representative value from said reference value is obtained as a correction factor in said correction-factor-obtaining step, the correction factor is added to the measured value(s) of the expression level(s) of the target small RNA(s);

(c) when a value calculated by dividing said representative value by said reference value is obtained as a correction factor in said correction-factor-obtaining step, the measured value(s) of the expression level(s) of the target small RNA(s) is/are divided by the correction factor; or (d) when a value calculated by dividing said reference value by said representative value is obtained as a correction factor in said correction-factor-obtaining step, the measured value(s) of the expression level(s) of the target small RNA(s) is/are multiplied by the correction factor.

(12) A device that corrects an expression level(s) of a target small RNA(s) for comparative analysis of the expression level(s) in a plurality of samples, said device comprising:

memory means that memorizes measured values of the expression level(s) of a target small RNA(s) in, and the amount(s) of a standard substance(s) extracted from, each of the samples, wherein said measured values are obtained by measurement using a nucleic acid sample obtained by adding at least one kind of standard substance to each of a plurality of samples, said standard substance being a nucleic acid with a nucleic acid length of not less than 200 bases, and then extracting nucleic acids from each of the samples;

representative-value-obtaining means that obtains, for each of the samples, a representative value from the measured value(s) of the amount(s) of the standard substance(s) extracted;

correction-factor-obtaining means that obtains, as a correction factor for each sample for correction of the expression level(s) of the target small RNA(s) in said each sample, the difference or the ratio between a reference value arbitrarily set in connection with the amount(s) of the standard substance(s) extracted and the representative value obtained for said each sample by said representative-value-obtaining means; and correction means that corrects the expression level(s) of the target small RNA(s) measured in each sample using each correction factor obtained by said correction-factor-obtaining means.

(13) The device according to (12), wherein said representative value is an average or a median expressed as a logarithmic value calculated from the measured value(s) of the amount(s) of the at least one standard substance extracted.

(14) The device according to (12) or (13), wherein the target small RNA is miRNA.

(15) The device according to any one of (12) to (14), wherein said correction is carried out by said correction means as follows:

(a) when a value calculated by subtracting said reference value from said representative value is obtained as a correction factor by said correction-factor-obtaining means, the correction factor is subtracted from the measured value(s) of the expression level(s) of the target small RNA(s);

(b) when a value calculated by subtracting said representative value from said reference value is obtained as a correction factor by said correction-factor-obtaining means, the correction factor is added to the measured value(s) of the expression level(s) of the target small RNA(s);

(c) when a value calculated by dividing said representative value by said reference value is obtained as a correction factor by said correction-factor-obtaining means, the measured value(s) of the expression level(s) of the target small RNA(s) is/are divided by the correction factor; or (d) when a value calculated by dividing said reference value by said representative value is obtained as a correction factor by said correction-factor-obtaining means, the measured value(s) of the expression level(s) of the target small RNA(s) is/are multiplied by the correction factor.

(16) The device according to any one of (12) to (15), wherein said measured values of the expression level(s) of the target small RNA(s) and the amount(s) of the standard substance(s) extracted in the plurality of samples that are memorized in said memory means are values obtained by carrying out hybridization by bringing each nucleic acid sample labeled with a labeling substance into contact with probes for capturing a plurality of target small RNAs and a probe(s) for capturing at least one standard substance, said probes being immobilized on a support, and obtaining the expression levels of the target small RNAs and the amount (s) of the standard substance(s) extracted, as signal intensity measurement values.

(17) A program(s) that corrects expression level(s) of a target small RNA(s) for comparative analysis of the expression level(s) among a plurality of samples, said program(s) causing one or more computers to execute:

a measurement step of measuring the amounts of the target small RNA(s) and the standard substance(s) present in each nucleic acid sample obtained by adding at least one kind of standard substance to each of the plurality of samples, said standard substance being a nucleic acid with a nucleic acid length of not less than 200 bases, and then extracting nucleic acids from each of the samples, to obtain measured values of the expression level(s) of the target small RNA(s) and the amount(s) of the standard substance(s) extracted;

a representative-value-obtaining step of obtaining, for each of the samples, a representative value from the measured value(s) of the amount(s) of the standard substance(s) extracted;

a correction-factor-obtaining step of obtaining, as a correction factor for each sample for correction of the expression level(s) of the target small RNA(s) in said each sample, the difference or the ratio between a reference value that is arbitrarily set in connection with the amount(s) of the standard substance(s) extracted and the representative value of the standard substance(s) obtained for said each sample in the representative-value-obtaining step; and a correction step of correcting the expression level(s) of the target small RNA(s) measured in each sample using the correction factor obtained for said each sample.

(18) A program(s) that corrects expression level(s) of a target small RNA(s) for comparative analysis of the expression level(s) among a plurality of samples, said program(s) causing one or more computers to function as:

memory means that memorizes measured values of the expression level(s) of the target small RNA(s) in, and the amount(s) of a standard substance(s) extracted from, each of the samples, wherein said measured values are obtained by measurement using a nucleic acid sample obtained by adding at least one kind of standard substance to each of the plurality of samples, said standard substance being a nucleic acid with a nucleic acid length of not less than 200 bases, and then extracting nucleic acids from each of the samples;

representative-value-obtaining means that obtains, for each of the samples, a representative value from the measured value(s) of the amount(s) of the standard substance(s) extracted;

correction-factor-obtaining means that obtains, as a correction factor for each sample for correction of the expression level(s) of the target small RNA(s) in said each sample, the difference or the ratio between a reference value that is arbitrarily set in connection with the amount(s) of the standard substance(s) extracted and the representative value obtained for said each sample by said representative-value-obtaining means; and correction means that corrects the expression level(s) of the target small RNA(s) measured in each sample using each correction factor obtained by said correction-factor-obtaining means.

(19) A computer-readable recording medium in which the program(s) according to (17) or (18) is/are recorded.

(20) A chip for analysis of small RNA expression, comprising a support on which probes capturing a plurality of target small RNAs and a probe(s) capturing at least one standard substance selected from standard substances that are nucleic acids whose base sequences are SEQ ID Nos:1 to 5 and 15 to 17 are immobilized.

When the expression levels of small RNAs extracted from samples are measured and compared among the samples, we make it possible to correct the expression levels of the small RNAs more accurately than conventional methods. Hence, we make it possible to carry out comparative analysis of the target small RNAs among the samples more accurately.

DESCRIPTION OF SYMBOLS

Figures 1A, 1B, 1C:
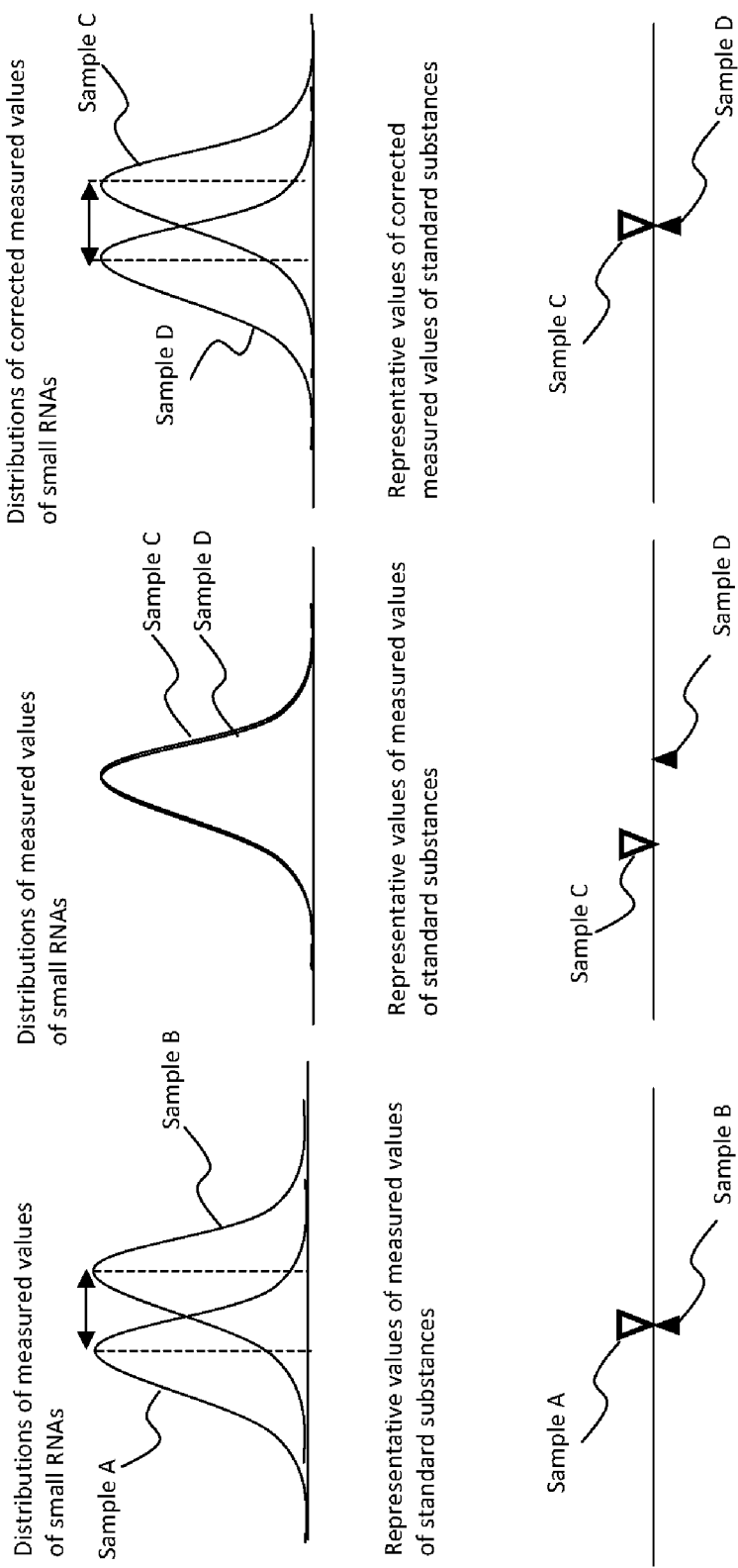
FIGS. 1A-1C are conceptual diagrams illustrating our method.

10 Analysis device
110 Input unit
120 Display unit
130 Output unit
140 Memory unit
150 Control unit
160 Conversion unit
170 Analysis unit

DETAILED DESCRIPTION

The standard substance is a substance to be used to obtain a reference to correct fluctuation (variation or errors among the measurements) of measured values of the expression level(s) of a target small RNA(s) among measurements on a plurality of samples, by allowing the standard substance to coexist stably in the samples containing the target small RNA(s) during the process from the extraction step to the measurement step and carrying out measurement of the expression level(s) of the small RNA(s) of interest together with measurement of the abundance of the standard substance. That is, measured values of the expression level(s) of a target small RNA(s) can be corrected among measurements on a plurality of samples using the abundance of the standard substance as a reference.

First, the concept of the method of correction of the expression level(s) of the target small RNA(s) using the standard substance is explained below based on FIGS. 1A-1C.

FIGS. 1A-1C show histograms of signal values, which schematically illustrate results of detection of nucleic acid extracted from samples and then labeled, which detection was carried out using a microarray on which probes to capture a plurality of kinds of target small RNAs (hereinafter also referred to as "small RNA-capture probes") and probes to capture standard substances (hereinafter also referred to as "standard substance-capture probes") are immobilized. The probes that capture small RNAs or the probes that capture standard substances are hereinafter also collectively referred to as "capture probes" or, simply, "probes".

FIG. 1A shows histograms illustrating results of DNA microarray analysis of target small RNAs extracted from Sample A and Sample B, respectively. The distributions (histograms) of measured values obtained from a plurality of target small RNA-capture probes loaded on the microarray, and the representative values of measured values obtained from a plurality of standard substance-capture probes are shown. Sample A and Sample B show histograms of small RNAs largely shifted from each other. Thus, it can be interpreted that there is a large difference in the expression levels of the small RNAs between the samples. On the other hand, another interpretation is possible: the difference could be due to an experimental error, especially due to difference in nucleic acid extraction efficiencies in the step of nucleic acid extraction from the samples. It is impossible to determine which interpretation is correct based merely on the histograms.

In FIG. 1A, the representative value of the measured values obtained from the probes for capturing standard substances that are nucleic acids is almost the same between Sample A and Sample B. That is, it can be determined that Sample A and Sample B were correctly subjected to the experiment, and hence that there is no experimental error. In such a case, it follows that there is a large difference in the expression levels of the small RNAs between Samples A and B, and that correction of the measured values of the small RNAs is unnecessary for comparison between the samples.

FIG. 1B schematically shows results of analysis of Sample C and Sample D using a DNA microarray. Histograms of measured values obtained from small RNA-capture probes, and the representative values of measured values obtained from standard substance-capture probes are shown.

Histograms of measured values of small RNAs from Sample C and Sample D show similar distributions. On the other hand, the representative values of the measured values obtained from the standard substance-capture probes are largely shifted from each other between Sample C and Sample D. Thus, it can be understood that the detection results from Sample C and Sample D include an experimental error due to some reason. In such a case, the measured values of the small RNAs need to be appropriately corrected for comparison between Samples C and D.

Histograms after correction of the measured values of the target small RNAs are shown in FIG. 1C. The specific method of the correction is as described later. The data from Sample C were corrected such that the measured values obtained from the standard substance-capture probes became consistent between Sample C and Sample D. As a result of this correction, the representative value of the measured values obtained from the standard substance-capture probes becomes consistent between Sample C and Sample D, and the histograms of the measured values from the target small RNA-capture probes corrected using the same correction factor come to be largely shifted from each other. That is, it follows that there is a large difference in the expression levels of the small RNAs also between Samples C and D.

Comparative analysis (measurements) of the expression level(s) of a target small RNA(s) is carried out among a plurality of samples. The number of the samples may be two, or may be three or more. The measurements among a plurality of samples herein include measurements of a plurality of different kinds of target small RNAs, measurements of respective samples when the same target small RNA is measured a plurality of times, and the combination of these.

The "small RNA" means an RNA having a base length of less than 200 bases that is produced in a living body. Examples of the small RNA include, but are not limited to, ribosomal RNA (5S rRNA, 5.8S rRNA), transfer RNA (tRNA), small nuclear ribonucleoprotein particle RNA (snoRNA), small nuclear RNA (snRNA), and microRNA (miRNA); and, as immature miRNAs before undergoing processing, stem-loop-shaped pre-miRNA and double-stranded miRNA/miRNA duplex. Preferred examples of the small RNA include miRNA.

Standard Substance

In the extraction step and the measurement step for comparative analysis of the expression level(s) of a target small RNA(s), a standard substance(s) is/are present at a predetermined content(s) with respect to the target small RNA(s). In particular, in the extraction step, it is preferred that the standard substance that is a nucleic acid be extracted with the same extraction efficiency as the target small RNA(s).

The standard substance is a nucleic acid. The nucleic acid length is longer than that of the target small RNA, and is not less than 200 bases, preferably 200 bases to 1200 bases, more preferably 500 bases to 1200 bases. In general, when a single-stranded RNA has a nucleic acid length of not less than 200 to 300 bases, formation of hydrogen bonds in the chain tends to occur easily, leading to physical stability of the RNA, as well as a chemically stable state of the RNA can also be maintained by its association with one or more of salts, lipids, proteins, and the like. On the other hand, when the nucleic acid length of the standard substance that is a nucleic acid is less than 200 bases, the efficiency of extraction from the samples and the measurement results may largely vary depending on the conditions for the extraction, sample conditions, and impurities contained in the samples, and in particular, there is a concern that the standard substance may be extracted with an extraction efficiency different from that of the small RNA(s).

The standard substance preferably has properties (1) and (2).
(1) The GC content is 30 to 70%.
(2) The Tm value is 10° C. to 95° C.

The GC content referred to in (1) can be determined from the abundance of G and C among all bases, that is, A, T, G, and C, in the base sequence of the standard substance used. The higher the GC content, the higher the number of hydrogen bonds, and thus the structure and the properties of the nucleic acid tend to be stable. However, when the GC content is too high, the sequence specificity in the measurement is lowered. Thus, the GC content of the standard substance is preferably 30 to 70%, more preferably 40 to 60%.

The Tm value referred to in (2) can be calculated based on the base sequence of the standard substance, using the Nearest Neighbor method (PNAS, 1998, 95: 1460-1465) or the like. It is generally said that the structural stability increases as the Tm value increases. Thus, the Tm value of the standard substance is preferably 10° C. to 95° C., more preferably 30° C. to 95° C., still more preferably 86° C. to 95° C.

Taking the measurement step into account, it is preferred that one that does not cross-hybridize with the gene transcripts contained in the samples used be selected as a standard substance to be used. More specifically, a nucleic acid having a sequence homology of not more than 50% to all the gene transcripts of the biological species in which the target small RNA(s) is/are to be measured deposited in a public database may be selected utilizing a homology search program. Examples of the homology search program that may be applied include, but are not limited to, public programs such as FASTA, BLAST, and Mega Blast. Examples of the public database include, but are not limited to, databases such as Genbank (NCBI), EMBL (EBI), Ensembl, and miRbase, which store sequence information of gene transcripts.

The standard substance can be prepared by application of an organic chemical synthesis method for nucleic acid, or by application of a biological synthesis method, for example, a method in which the standard substance is synthesized in a host microorganism such as *E. coli* using a vector prepared by incorporating the sequence of the standard substance into a plasmid or the like, or a method in which a sequence that can be recognized by RNA polymerase such as a T7 promoter is incorporated upstream of the sequence of the standard substance, and synthesis of the standard substance is carried out with an enzyme such as T7 polymerase. Further, nucleic acid standard substances that can be used as standards for evaluation of the validity of an analysis device or an analysis method or for accuracy control of such a device or analysis method are known, and there are also commercially available products of such nucleic acid standard substances. These known substances may also be used as standard substances.

Examples of the standard substance include not only those in the form of a single strand, but also those in the form of a double strand formed with the complementary strand. For the purpose of matching the chemical properties with those of the target small RNA(s), the standard substance may contain a base sequence of a naturally occurring nucleic acid as part of its sequence, or may contain a base sequence that is not naturally present. The standard substance may have a sequence in which an identical base sequence is repeated a plurality of times or randomly arranged a plurality of times. A start codon and/or a stop codon may be contained as part of the sequence. The sequence may also have a primer site(s) such as poly(A) at one or both sides of the sequence.

Although the standard substance is preferably DNA or RNA, a nucleic acid derivative such as an artificial nucleic acid including PNA and LNA may also be used. The "nucleic acid derivative" herein means a derivative such as a labeled derivative that is labeled with a fluorophore or the like, or a derivative containing a modified nucleotide (for example, a nucleotide containing halogen, or containing a group such as alkyl including methyl; alkoxy including methoxy; thio; or carboxymethyl; or a nucleotide that has undergone reconstruction of the base, saturation of a double bond(s), deamination, substitution of an oxygen molecule(s) into a sulfur molecule(s), and/or the like). In addition, each end may be modified with various functional groups. Examples of such a functional group include the phosphate group, amino group, and thiol group.

In the method, one or more kinds of standard substances may be used. The standard substance may be used in a state where it is associated with a protein, or in a state where it is included in a vesicle formed with lipids.

Samples

Examples of the sample which can be used in the method include, but are not limited to, samples separated from living bodies, i.e. biological samples such as various tissue fluids and body fluids including blood, serum, plasma, urine, feces, spinal fluid, saliva, swab, cerebrospinal fluid, sweat, lacrimal fluid, seminal fluid, lymph, and synovial fluid; frozen samples and paraffin-embedded samples (FFPEs) of various tissues and cells, and sections thereof; and culture liquids obtained by culturing cells or tissues. Examples of the sample also include various foods and beverages as well as dilutions thereof. The sample is especially preferably a body fluid since a predetermined amount of the standard substance is added to a predetermined amount of the sample. The plurality of samples to be subjected to the comparative analysis may be a plurality of samples derived from different tissues, a plurality of samples derived from the same tissue separated from different living bodies, or a plurality of samples derived from different sites (for example, from a lesion site such as a tumor, and a non-lesion site) of the same tissue.

Addition of Standard Substance to Samples

In the method, a predetermined amount of standard substance is added to a predetermined amount of sample. The unit of the amount in this case is not limited, and may be either the weight or the volume. When a predetermined amount of standard nucleic acid solution is added, the unit for measurement of the predetermined amount of the standard substance solution may be any unit such as the weight, volume, or number of moles. Examples of the method of measuring the amount of the standard substance include various known methods such as the absorbance measurement method, electrophoresis method, column method, and capillary electrophoresis method.

Before extraction of the nucleic acid, a predetermined amount of the standard substance is added to a predetermined amount of the sample. Preferably, the sample is mixed with an extraction solution, and nucleases that may be present in the sample are deactivated with a guanidinium salt or the like, and thereafter the standard substance is added to the sample. The standard substance is more preferably added before the separation of a solution containing RNA.

When the standard substance is added to the sample, the standard substance may be either in a solution state or in a dry solid state. For accurate addition of a predetermined amount of the standard substance, it is preferably added in a solution state, more preferably added in an amount of several microliters to several hundred microliters. When the standard substance is added as a solution, a pipette is usually used. However, accurate measurement of a volume in the order of below microliters is difficult, while a volume in the order of milliliters or more is too much against the volume of the sample, resulting in a significant change in the composition of the extraction solution so that the subsequent extraction operation may be largely influenced. When preparing a solution of the standard substance, water or a buffer such as PBS is preferably used as a solvent for the solution.

The amount of the standard substance added to the sample is preferably one which makes the final concentration of the standard substance become almost the same as the concentration of the target small RNA contained in the sample. The concentration of the small RNA contained varies depending on the type of the sample. In a body fluid, the standard substance is added to the sample to a concentration in the order of z(zepto)mol/mL to p(pico)mol/mL, more preferably in the order of a(atto)mol/mL to f(femto)mol/mL. Examples of the method of measuring its concentration include the absorbance measurement method, fluorescence method, electrophoresis method, column method, and capillary electrophoresis method.

After the nucleic acid extraction, the resulting extract may be subjected to measurement by the absorbance measurement method, fluorescence method, electrophoresis method, column method, capillary electrophoresis method or the like to confirm the presence of the target small RNA(s) and the standard substance(s), or to measure their amounts.

Extraction Step

A treatment of extraction of nucleic acids containing the target small RNA(s) from each sample (extraction step) is carried out in the presence of the standard substance(s). Since the standard substance(s) added to each sample is extracted together with the target small RNA(s), the nucleic acid sample obtained from each sample in this extraction step contains the target small RNA(s) and the standard substance(s).

As the method of extracting the nucleic acids from the sample, various known methods may be used. It is preferred to use the AGPC method and the phenol/chloroform method, which are commonly used as methods to extract RNA. In such cases, the extraction solution is preferably a solution containing 2 to 5 M guanidine and 40 to 60% phenol. As an extraction solution which allows effective removal of impurities such as proteins, an extraction solution containing, with respect to the total amount of the extraction solution, (a) more than 50 vol % phenol;
(b) 3 to 10 vol % polyhydric alcohol with respect to the total amount of the solution;

(c) 0.5 to 2.0 M guanidinium salt with respect to the total amount of the solution;

(d) 0.1 to 0.5 M thiocyanate with respect to the total amount of the solution; and (e) a buffering agent for maintaining the pH of the solution at 4 to 6; is preferably used. Further, various salts may be added to the extraction solution for easy extraction of nucleic acids.

Specific examples of the extraction step that may be applied include a method in which the sample is homogenized in the extraction solution to form a homogenate, and an organic solvent for separating an aqueous solution containing RNA is added to the homogenate, followed by centrifuging the resulting mixture. In such a process, as described above, it is preferred to add the standard substance(s) after mixing the sample with the extraction solution but before the centrifugation.

The solution containing the extracted small RNA may be purified by further subjecting it to one or more of processes such as precipitation, chromatography, centrifugation, electrophoresis, and affinity separation. For example, as a precipitation process, a process in which a lower alcohol is added to the solution containing the small RNA to precipitate the small RNA, and the precipitated small RNA is collected, may be employed. As a chromatography process, a process in which a lower alcohol is added to the solution containing the small RNA to precipitate the small RNA, and the precipitated small RNA is adsorbed to a carrier which can adsorb RNA such as a silica membrane column, followed by eluting the small RNA from the carrier (column) and collecting the small RNA, may be employed.

Measurement Step

The amounts of a target small RNA(s) and a standard substance(s) contained in nucleic acid samples extracted from a plurality of samples by the above-described extraction step are measured (measurement step).

Examples of the measurement method employed include various methods such as amplification methods including the PCR method and sequencing; and hybridization methods including the Northern hybridization method, Southern hybridization method, and array method. Among the hybridization methods, an array method using an array chip such as a microarray on which probes that specifically bind to the RNA(s) of interest and the standard substance(s) are immobilized is preferably used to carry out the measurement. More specifically, an array chip containing a support on which a target small RNA-capture probe(s) and a standard substance-capture probe(s) are aligned and immobilized may be preferably used.

The "capture probe" or the "probe for capturing" means a substance capable of directly or indirectly, preferably directly, and selectively binding to the nucleic acid such as RNA to be captured. Representative examples of such a probe include nucleic acids, proteins, sugars, and other antigenic compounds. Nucleic acid probes may preferably be used. The nucleic acid probe can be prepared using DNA or RNA, or a nucleic acid derivative such as PNA (peptide nucleic acid) or LNA (Locked Nucleic Acid). The "nucleic acid derivative" herein means a derivative such as a labeled derivative that is labeled with a fluorophore or the like, or a derivative containing a modified nucleotide (for example, a nucleotide containing halogen, or containing a group such as alkyl including methyl; alkoxy including methoxy; thio; or carboxymethyl; or a nucleotide that has undergone reconstruction of the base, saturation of a double bond(s), deamination, substitution of an oxygen molecule(s) into a sulfur molecule(s) and/or the like).

From the viewpoint of securing stability in the hybridization, the base length of the nucleic acid probe is preferably not less than 20 bases. Usually, when the chain length is about 20 to 100 bases, the probe can sufficiently exert the selective binding capacity to the subject RNA. Such an oligonucleic acid probe having a short chain length can be easily prepared by a well-known chemical synthesis method or the like.

The nucleic acid probe preferably has the base sequence completely complementary to the subject nucleic acid (the target small RNA or the standard substance which is a nucleic acid). However, even when there is a partial difference in the base sequence, the nucleic acid probe can be used as the capture probe as long as the nucleic acid probe has a base sequence which is homologous enough to allow hybridization with the subject nucleic acid under stringent conditions.

The stringency in the hybridization is known to be a function of the temperature, the salt concentration, the chain length of the probe, the GC content of the nucleotide sequence of the probe, and the concentration of the chaotropic agent in the hybridization buffer. As the stringent conditions, those described in "Sambrook, J. et al., Molecular Cloning: A Laboratory Manual (2nd ed.), Cold Spring Harbor Laboratory Press, New York (1998)" or the like may be employed. The stringent temperature condition is not less than about 30° C. Examples of other conditions include the hybridization time, the concentration of the washing agent (for example, SDS), and the presence or absence of carrier DNA. By combining these conditions, various stringencies can be set. Those skilled in the art can appropriately determine conditions under which the nucleic acid probes provided to detect the target small RNA(s) contained in the desired samples and the standard substance(s) used can appropriately exert their function as capture probes.

Sequence information of small RNAs can be obtained from databases such as GenBank. Sequence information of miRNA can be obtained from, for example, the website of miRbase. The small RNA-capture nucleic acid probe(s) can be designed based on sequence information available from these sites.

The number of the small RNA-capture probes immobilized on the support is not limited. For example, an array in which a sufficient number of the small RNA-capture probes that comprehensively cover all known miRNAs whose sequences have been identified are immobilized on a support may be used to measure the expression level(s) of the small RNA(s), or an array in which a capture probe(s) for a desired number of small RNA(s) is/are immobilized on a support may be used. For example, one or more particular small RNA-capture probes associated with a particular disease or particular biological conditions may be used.

The probe that captures the standard substance is not limited as long as it can complementarily capture the standard substance used. Preferably, the probe has a homology of not less than 50% to the base sequence of the standard substance, and does not form a higher-order structure. For example, the probe can be designed by the method described in JP 2011-239708 A.

As the support on which the capture probes are immobilized, those which are the same as supports used in known microarrays, macroarrays and the like may be used. Examples of the support include slide glasses, membranes, and beads. The support described in JP 4244788 B, which has a plurality of protruded portions on its surface, may also be used. Examples of the material of the support include, but are not limited to, inorganic materials such as glass, ceramic, and silicone; and polymers such as polyethylene terephthalate, cellulose acetate, polycarbonate, polystyrene, polymethyl methacrylate, and silicone rubber.

Examples of the known methods of immobilizing capture probes on a support include methods in which oligo-DNAs are synthesized on the surface of the support, and methods in which oligo-DNAs preliminarily synthesized are added dropwise to the surface of the support and then fixed thereon.

Examples of the former methods include the method of Ronald (U.S. Pat. No. 5,705,610 B), the method of Michel (U.S. Pat. No. 6,142,266 B), and the method of Francesco (U.S. Pat. No. 7,037,659 B). In those methods, an organic solvent is used in the DNA synthesis reaction and, therefore, the material of the support is preferably a material resistant to organic solvents. In the method of Francesco, the DNA synthesis is controlled by irradiation with light from the back side of the support, and therefore the material of the support needs to be a light-transmitting material.

Examples of the latter methods include the method of Hirota (JP 3922454 B) and methods using a spotter. Examples of the spotting method include the pin method based on mechanical contact of a pin tip with a solid phase; the ink jet method utilizing the principle of ink jet printers; and the capillary method, which uses a capillary. If necessary, after the spotting treatment, post-treatment such as cross-linking by UV irradiation and/or surface blocking is carried out. To allow immobilization of the oligo-DNAs through covalent bonds on the surface of the surface-treated support, functional groups such as amino groups and/or SH groups are introduced to the termini of the oligo-DNAs. The surface modification of the support is usually carried out by treatment with a silane coupling agent having an amino group and/or the like.

To detect one kind of small RNA or standard substance, its capture probe may be immobilized on a plurality of immobilization areas on the support. For example, the same capture probe to capture one kind of small RNA or standard substance may be immobilized on a plurality of sites on the support, or, when a plurality of kinds of capture probes can be designed for one kind of small RNA or standard substance, the plurality of kinds of capture probes may be immobilized on the support for targeting the same small RNA or standard substance.

The hybridization with each probe immobilized on the support is carried out by binding a labeling substance to a nucleic acid sample extracted from a sample to which at least one standard substance was added, to prepare a nucleic acid sample labeled with the labeling substance, and then bringing the labeled nucleic acid sample into contact with the probes. The term "nucleic acid sample" includes not only RNA extracted from a sample, but also cDNA and cRNA prepared from the RNA by reverse transcription reaction. Thus, the labeled nucleic acid sample may be a sample prepared by directly or indirectly labeling a target small RNA(s) and a standard substance(s) in a nucleic acid sample with a labeling substance, or a sample prepared by directly or indirectly labeling cDNA or cRNA prepared from RNA (which includes cDNA or cRNA prepared from the target small RNA(s) and the standard substance(s) by reverse transcription reaction when the standard substance is RNA) in a nucleic acid sample with a labeling substance.

Examples of the method of binding the labeling substance to the nucleic acid sample include methods in which the labeling substance is bound to the 3'-end of the nucleic acid sample, methods in which the labeling substance is bound to the 5'-end of the nucleic acid sample, and methods in which a nucleotide to which the labeling substance is bound is incorporated into the nucleic acids. In the methods in which the labeling substance is bound to the 3'-end and the methods in which the labeling substance is bound to the 5'-end, enzymatic reaction may be used. In the enzymatic reaction, T4 RNA Ligase, Terminal Deoxitidil Transferase, Poly A polymerase, or the like may be used. Any of the labeling methods may be carried out by reference to the methods described in "Shao-Yao Ying (ed.), miRNA Experimental Protocols, Yodosha Co., Ltd. (2008)". Various kits to directly or indirectly bind labeling substances to RNA termini are commercially available. Examples of kits to directly or indirectly bind a labeling substance to the 3'-end include miRCURY miRNA HyPower labeling kit (Exiqon), NCode miRNA Labeling system (Life Technologies), and FlashTag Biotin RNA Labeling Kit (Genisphere). In the NCode miRNA Labeling system provided by Life Technologies, a poly(A) tail is attached to miRNA, and a capture sequence is ligated to the 3'-end using a cross-linking oligo (dT), followed by hybridizing the resulting product with an array and then adding a labeling substance having a sequence that hybridizes with the capture sequence, to achieve labeling of the miRNA through the capture sequence. Thus, this method is a method of indirectly binding a labeling substance to miRNA. Labeling can be carried out by these methods when RNA having a phosphorylated 3'-end is used as the standard substance(s).

In addition to the above, the same method as the conventional methods may also be used. That is, cDNA or cRNA may be synthesized from RNA extracted from a sample in the presence of labeled deoxyribonucleotides or labeled ribonucleotides to prepare cDNA or cRNA in which a labeled substance is incorporated, and the resulting cDNA or cRNA may be hybridized with the probes on the array. This method can be employed when RNA is used as the standard substance(s).

A plurality of samples are used. The same labeling substance may be used for all of the samples, or a plurality of different labeling substances may be used.

Examples of labeling substances that may be used include various labeling substances that are also used in known microarray analyses. Specific examples of the labeling substances include, but are not limited to, fluorescent dyes, phosphorescent dyes, enzymes, and radioisotopes. Fluorescent dyes are preferred since they can be easily measured and their signals can be easily detected. Specific examples of the fluorescent dyes include, but are not limited to, known fluorescent dyes such as Cyanine (Cyanine 2), aminomethylcoumarin, fluorescein, indocarbocyanine (Cyanine 3), Cyanine 3.5, tetramethylrhodamine, rhodamine red, Texas red, indocarbocyanine (Cyanine 5), Cyanine 5.5, Cyanine 7, and Oyster.

As the labeling substance, luminescent semiconductor particles may also be used. Examples of such semiconductor particles include cadmium selenium (CdSe), cadmium tellurium (CdTe), indium gallium phosphide (InGaP), and silver indium zinc sulfide (AgInZnS).

The thus labeled nucleic acid sample containing nucleic acids derived from a sample (target small RNA) and a standard substance, is brought into contact with the probes on the support to allow hybridization. This hybridization step may be carried out in completely the same manner as the conventional hybridization step. The reaction temperature and the reaction time are appropriately selected depending on the chain length of the nucleic acid to be subjected to the hybridization. In nucleic acid hybridization, hybridization is usually carried out at about 30° C. to 70° C. for 1 minute to ten and several hours. After the hybridization and the washing, the signal intensity from the labeling substance in each area where each probe is immobilized on the substrate is detected. Detection of the signal intensity is carried out using an appropriate signal reader selected depending on the type of the labeling substance. When a fluorescent dye is used as the labeling substance, a fluorescence microscope or a fluorescence scanner may be used.

The detected measured value (signal value) is compared with the surrounding noise. More specifically, the measured value obtained from the probe-immobilized area and the measured value obtained from a position other than the probe-immobilized area are compared with each other and, when the former value is higher than the latter value, the signal intensity is regarded as being detected (effectively judged positive).

When the background noise is included in the detected measured value, the background noise may be subtracted from the detected measured value. The surrounding noise may be regarded as the background noise, and may be subtracted from the detected signal value. In addition, the method described in "Microarray data statistical analysis protocols (Yodosha Co., Ltd.)" may be used.

By the above-described process, the amounts of the target small RNA(s) and the standard substance(s) present in each nucleic acid sample, that is, measured values of the expression level(s) of the target small RNA(s) in, and the amount(s) of the standard substance(s) extracted from, each sample, are obtained as signal intensities.

Representative-Value-Obtaining Step

Subsequently, in the method, a representative value is obtained for each sample from the measured value(s) of the abundance(s) of the standard substance(s) in the extracted nucleic acid sample (representative-value-obtaining step). The term "abundance of a standard substance in a nucleic acid sample" has the same meaning as the term "amount of a standard substance extracted from a sample". The terms "abundance of a standard substance" and "amount of a standard substance extracted" are used in the same meaning. The abundance of a standard substance in a nucleic acid sample or the amount of a standard substance extracted from a sample may also be simply referred to as "amount of a standard substance". That is, the term "amount of a standard substance in a sample" does not mean the amount of the standard substance added to the sample, but means the abundance of the standard substance in the nucleic acid sample or the amount of the standard substance extracted from the sample.

When one kind of standard substance is used, the measured value of the one kind can be the representative value. When two or more kinds of standard substances are used, the representative value may be obtained by any of the following various methods.

Typical examples of the representative value include the average and the median. The average means the average calculated from measured values of the amounts of a plurality of standard substances extracted (for example, measured values of signal intensities obtained using a microarray). The median means the median obtained from measured values of the amounts of a plurality of standard substances extracted (for example, measured values of signal intensities obtained using a microarray).

The average or the median may be an average or a median expressed as a logarithmic value. The "average expressed as a logarithmic value" means the average calculated from the logarithmic values obtained by converting measured values of the plurality of standard substances extracted (for example, measured values of signal intensities obtained using a microarray) to base 2 logarithms. The "median expressed as a logarithmic value" means the median of the logarithmic values obtained by converting measured values of the amounts of a plurality of standard substances extracted (for example, measured values of signal intensities obtained using a microarray) to base 2 logarithms, or means the logarithmic value obtained by conversion of the median of measured values of the amounts of a plurality of standard substances extracted to a base 2 logarithm. In the median, the same value can be obtained irrespective of whether the conversion of the measured values to logarithms is carried out in advance or later.

The average or the median may be calculated using all of the measured values of the plurality of standard substances that were measured, or may be calculated using only a part of the measured values selected from those obtained from the plurality of standard substances. For example, the average or the median may be calculated using all of the measured values obtained with the standard substance-capture probes loaded on a microarray, or may be calculated using a part of the standard substance-capture probes (for example, when 10 kinds of standard substance-capture probes are loaded on the microarray, 5 out of the 10 probes). For example, only a standard substance-capture probe(s) that was/were effectively judged positive across all the samples to be subjected to the comparative analysis may be selected and used to obtain the representative value of the standard substance. Before the calculation of the representative value, outliers may be excluded from the measured values of the abundances of the standard substances.

In some cases, a plurality of measured values are obtained for one standard substance when a plurality of kinds of capture probes are used for the one kind of standard substance or when the detection is carried out using an array in which one kind of capture probe is spotted on a plurality of sites. Also, in such cases, similarly to when two or more kinds of standard substances are used, an average or a median, for example, an average or a median expressed as a logarithmic value, calculated from the plurality of measured values can be used as the representative value. All of the measured values may be used to calculate the representative value, or only part of the measured values may be used to calculate the representative value.

In a mode in which a plurality of standard substances are used, when one kind of capture probe is spotted on a plurality of sites for each standard substance on an array, the average of the measured values of the signals from the plurality of capture probe spots may be calculated for each standard substance, and each average may be logarithmically converted, followed by obtaining the average or the median among the plurality of standard substances using each logarithmic value. The thus calculated average or median is also included in the "average or median expressed as a logarithmic value".

The CV (coefficient of variation) value of the representative values for a plurality of samples is preferably not more than 0.5. Normally, the CV value of the measured values when a microarray is used is not more than 0.5. When the CV value is not less than 0.5, there is a large variation, and the efficiency of extraction of the standard substance(s) in the extraction step is unstable so that it is assumed that the accuracy of the data after the correction may be lowered as a result.

Correction-Factor-Obtaining Step

Subsequently, using the representative value of the amount(s) of the standard substance(s) extracted obtained in the representative-value-obtaining step for each sample and a reference value arbitrarily set for the amount(s) of the standard substance(s) extracted, a correction factor to be used for correction of the expression level(s) of the target small RNA(s) is obtained (correction-factor-obtaining step). In this correction-factor-obtaining step, the correction factor may be calculated using the difference between the representative value and the reference value, or may be calculated using the ratio between the representative value and the reference value. When a representative value that is not logarithmically converted is used, it is preferred, but not necessarily required, to calculate the correction factor using the ratio and, when a representative value expressed as a logarithm is used, it is preferred, but not necessarily required, to calculate the correction factor using the difference. These two kinds of steps are described below.

Correction-Factor-Obtaining Step-1

The correction-factor-obtaining step-1 is a process utilizing the difference between the representative value of the amount(s) of the standard substance(s) extracted and the reference value. To this step, the following 1-1. reference sample-obtaining method or 1-2. fixed-value correction method may be applied.

1-1. Reference Sample-Obtaining Method

One sample (first sample) is arbitrarily selected from a plurality of samples to be analyzed, which sample is used as a "reference sample". The remaining one or more samples (subsequent sample(s)) are provided as a "sample(s) to be corrected".

The term "subsequent sample(s)" includes the second sample. For example, when the number of the plurality of samples to be compared is two, the sample to be corrected is only the second sample and, when the number of the plurality of samples to be compared is three, there are two samples to be corrected, that is, the second sample and the third sample.

In this method, the representative value of the amount(s) of the standard substance(s) in the reference sample is used as the "reference value". The difference between the reference value and the representative value of the amount(s) of the standard substance(s) in a certain one of the subsequent sample(s) (sample(s) to be corrected) is used as the correction factor for the certain one of the subsequent sample(s). Thus, the number of the correction factors obtained is the same as the number of the samples to be corrected.

More specifically, the correction factor is calculated according to Equation 1 or Equation 1'.

$c_{1\text{-}1}$=(representative value of amount(s) of standard substance(s) in reference sample (reference value))−(representative value of amount(s) of standard substance(s) in sample to be corrected) (1)

$c_{1\text{-}1'}$=(representative value of amount(s) of standard substance(s) in sample to be corrected)−(representative value of amount(s) of standard substance(s) in reference sample (reference value)) (1')

For example, when measurement of the expression levels is carried out using a microarray, and the average expressed as a logarithmic value is used as the representative value of the amount(s) of the standard substance(s), the correction factor for the sample to be corrected can be calculated according to Equation 2 or Equation 2'.

$$c_{1\text{-}1} = \frac{1}{n}\sum_{j=1}^{n} \log_2 Aj - \frac{1}{n}\sum_{j=1}^{n} \log_2 Xj \quad (2)$$

$$c_{1\text{-}1'} = \frac{1}{n}\sum_{j=1}^{n} \log_2 Xj - \frac{1}{n}\sum_{j=1}^{n} \log_2 Aj \quad (2')$$

In Equation 2 and Equation 2', n represents the total number of area(s) where standard substance-capture probe(s) is/are immobilized on the support;

Aj represents the signal measurement value from the jth ($1 \leq j \leq n$) area where a standard substance-capture probe is immobilized in the reference sample; and Xj represents the signal measurement value from the jth ($1 \leq j \leq n$) area where a standard substance-capture probe is immobilized in the second sample.

When the probe(s) and the standard substance(s) have a one-to-one relationship, n is equal to the number of the standard substance(s) targeted by the standard substance-capture probe(s) on the support.

In Equation 2 and Equation 2', n', the total number of area(s) where standard substance-capture probe(s) is/are immobilized that was/were effectively judged positive across all the samples to be compared, may be used instead of n.

1-2. Fixed-Value Correction Method

This method preliminarily assumes that the representative value of the amount(s) of the standard substance(s) is constant among all samples. That is, a fixed value is used as the "reference value", and the difference between this fixed value and the representative value of the amount(s) of the standard substance(s) in each sample is obtained. This difference is utilized as the correction factor. In this method, the "reference sample" described in 1-1. does not exist, and therefore all of the plurality of samples to be subjected to the comparative analysis are "samples to be corrected". Thus, the number of the correction factors obtained is the same as the number of the samples to be subjected to the comparative analysis.

More specifically, the correction factor is calculated according to Equation 3 or Equation 3'.

$r_{1\text{-}2}$=(fixed value (reference value))−(representative value of amount(s) of standard substance(s) in sample to be corrected) (3)

$r_{1\text{-}2'}$=(representative value of amount(s) of standard substance(s) in sample to be corrected)−(fixed value (reference value)) (3')

For example, when measurement of the expression levels is carried out using a microarray, and the average expressed as a logarithmic value is used as the representative value of the amount(s) of the standard substance(s), the correction factor for the sample to be corrected can be calculated according to Equation 4 or Equation 4'.

$$r_{1\text{-}2} = \alpha - \frac{1}{n}\sum_{j=1}^{n} \log_2 Yj \quad (4)$$

$$r_{1\text{-}2'} = \frac{1}{n}\sum_{j=1}^{n} \log_2 Yj - \alpha \quad (4')$$

In Equation 4 and Equation 4',

α represents the reference value (fixed value);

n represents the total number of area(s) where standard substance-capture probe(s) is/are immobilized on the support; and Yj represents the signal measurement value from the jth ($1 \leq j \leq n$) area where a standard substance-capture probe is immobilized in the sample.

When the probe(s) and the standard substance(s) have a one-to-one relationship, n is equal to the number of the standard substance(s) targeted by the standard substance-capture probe(s) on the support.

In Equation 2 and Equation 2', n', the total number of area(s) where standard substance-capture probe(s) is/are immobilized that was/were effectively judged positive across all the samples to be compared, may be used instead of n.

As the fixed value to be used as the reference value in the fixed-value correction method, any value (excluding 0) may be used as long as the same value is consistently used for all samples at least in one time of comparative analysis. By using the same expression measurement system, and always using the same value as the fixed value, comparative analysis can be carried out even between samples which were subjected to measurement of the expression levels on different days. For example, since the amount of each standard substance added to one sample is the same across all the samples, the fixed value may be determined based on the amount(s) of the standard substance(s) added. However, since the signal value detected may vary depending on the system used in the measurement step, the fixed value may be selected without limitation depending on the system used.

Correction-Factor-Obtaining Step-2

The correction-factor-obtaining step-2 is a process utilizing the ratio between the representative value of the amount(s) of the standard substance(s) and the reference value. To this step, the following 2-1. reference sample-obtaining method or 2-2. fixed-value correction method may be applied.

2-1. Reference Sample-Obtaining Method

One sample (first sample) is arbitrarily selected from a plurality of samples to be analyzed, which sample is used as a "reference sample". The remaining subsequent sample(s) is/are a "sample(s) to be corrected".

In this method, the representative value of the amount(s) of the standard substance(s) in the reference sample is used as a "reference value", and the ratio between the reference value and the representative value of the amount(s) of the standard substance(s) in a certain one of the subsequent sample(s) (sample(s) to be corrected) is used as the correction factor for the certain one of the subsequent sample(s). Thus, the number of the correction factors obtained is the same as the number of the samples to be corrected.

More specifically, the correction factor is calculated according to Equation 5 or Equation 5'.

$c_{2\text{-}1}$=(representative value of amount(s) of standard substance(s) in reference sample (reference value))/(representative value of amount(s) of standard substance(s) in sample to be corrected) (5)

$c_{2\text{-}1'}$=(representative value of amount(s) of standard substance(s) in sample to be corrected)/(representative value of amount(s) of standard substance(s) in reference sample (reference value)) (5')

For example, when measurement of the expression levels is carried out using a microarray, and the average expressed as a logarithmic value is used as the representative value of the amount(s) of the standard substance(s), the correction factor for the second sample can be calculated according to Equation 6 or Equation 6'.

$$c_{2\text{-}1} = \frac{1}{n}\sum_{j=1}^{n} \log_2 Aj \div \frac{1}{n}\sum_{j=1}^{n} \log_2 Xj \qquad (6)$$

$$c_{2\text{-}1'} = \frac{1}{n}\sum_{j=1}^{n} \log_2 Xj \div \frac{1}{n}\sum_{j=1}^{n} \log_2 Aj \qquad (6')$$

In Equation 6 and Equation 6', n represents the total number of area(s) where standard substance-capture probe(s) is/are immobilized on the support;

Aj represents the signal measurement value from the jth ($1 \leq j \leq n$) area where a standard substance-capture probe is immobilized in the reference sample; and Xj represents the signal measurement value from the jth ($1 \leq j \leq n$) area where a standard substance-capture probe is immobilized in the second sample.

When the probe(s) and the standard substance(s) have a one-to-one relationship, n is equal to the number of the standard substance(s) targeted by the standard substance-capture probe(s) on the support.

In Equation 6 and Equation 6', n', the total number of area(s) where standard substance-capture probe(s) is/are immobilized that was/were effectively judged positive across all the samples to be compared, may be used instead of n.

2-2. Fixed-Value Correction Method

This method preliminarily assumes that the representative value of the amount(s) of the standard substance(s) is constant among all samples. That is, a fixed value is used as the "reference value", and the ratio between this fixed value and the representative value of the amount(s) of the standard substance(s) in each sample is obtained. This ratio is utilized as the correction factor. In this method, the "reference sample" described in 2-1. does not exist, and therefore all of the plurality of samples to be subjected to the comparative analysis are "samples to be corrected". Thus, the number of the correction factors obtained is the same as the number of the samples to be subjected to the comparative analysis.

More specifically, the correction factor is calculated according to Equation 7 or Equation 7'.

$r_{2\text{-}2}$=(fixed value (reference value))/(representative value of amount(s) of standard substance(s) in sample to be corrected) (7)

$r_{2\text{-}2'}$=(representative value of amount(s) of standard substance(s) in sample to be corrected)/(fixed value (reference value)) (7')

For example, when measurement of the expression levels is carried out using a microarray, and the average expressed as a logarithmic value is used as the representative value of the amount(s) of the standard substance(s), the correction factor for the sample to be corrected can be calculated according to Equation 8 or Equation 8'.

$$r_{2\text{-}2} = \alpha \div \frac{1}{n}\sum_{j=1}^{n} \log_2 Yj \qquad (8)$$

$$r_{2\text{-}2'} = \frac{1}{n}\sum_{j=1}^{n} \log_2 Yj \div \alpha \qquad (8')$$

In Equation 8 and Equation 8',

α represents a fixed value;

n represents the total number of area(s) where standard substance-capture probe(s) is/are immobilized on the support; and Yj represents the signal measurement value from the jth (1≤j≤n) area where a standard substance-capture probe is immobilized in the sample.

When the probe(s) and the standard substance(s) have a one-to-one relationship, n is equal to the number of the standard substance(s) targeted by the standard substance-capture probe(s) on the support.

In Equation 8 and Equation 8', n', the total number of area(s) where standard substance-capture probe(s) is/are immobilized that was/were effectively judged positive across all the samples to be compared, may be used instead of n.

Details of the "fixed value" to be used here as the reference value are the same as those of the fixed value in "1-2. Fixed-Value Correction Method".

Correction Step

Subsequently, using the correction factor obtained by the correction-factor-obtaining step-1 or the correction-factor-obtaining step-2, correction of the expression level(s) of the target small RNA(s) in a sample(s) to be corrected is carried out utilizing the method of the correction step-1 or the correction step-2.

Correction Step-1

The correction step-1 is a process in which correction of the expression level(s) of the target small RNA(s) is carried out using the correction factor obtained in the correction-factor-obtaining step-1, and the correction is carried out by adding the correction factor to the expression level(s) of the target small RNA(s) or by subtracting the correction factor from the expression level(s). In this step, there are two ways of carrying out the correction: one corresponds to the reference sample-obtaining method, and the other corresponds to the fixed-value correction method, in the correction-factor-obtaining step-1.

1-1. Reference Sample-Obtaining Method

Correction of the expression level(s) of the target small RNA(s) in the subsequent sample(s) is carried out using the correction factor obtained for each one of the subsequent sample(s). That is, when the expression level(s) of the target small RNA(s) in the second sample is/are corrected, the correction factor for the second sample ($c2_{1-1}$ or $c2_{1-1}'$) is used and, when the expression level(s) of the target small RNA(s) in the third sample is/are corrected, the correction factor for the third sample ($c3_{1-1}$ or $c3_{1-1}'$) is used.

When the difference obtained by subtracting the representative value of the amount(s) of the standard substance(s) in each one of the subsequent sample(s) from the representative value of the standard substance(s) in the reference sample is used as the correction factor, that is, when Equation 1 is applied, each individual correction factor is added to the measured value(s) or the logarithmic value(s) of the measured value(s) of the expression level(s) of the target small RNA(s) in each one of the subsequent sample(s), thereby carrying out correction of the expression level(s) of the target small RNA(s) in each of the subsequent sample(s). In this case, the correction can be expressed as an equation as follows. That is, the corrected expression level Ei of the ith target small RNA in a "sample to be corrected" can be calculated according to Equation 9.

$$Ei = \log_2 Wi + c_{1-1} \quad (9)$$

Wi represents the signal measurement value from the area where the ith small RNA-capture probe is immobilized.

In contrast, when the difference obtained by subtracting the representative value of the standard substance(s) in the reference sample from the representative value of the amount(s) of the standard substance(s) in each one of the subsequent sample(s) is used as the correction factor, that is, when Equation 1' is applied, each individual correction factor is subtracted from the measured value(s) or the logarithmic value(s) of the measured value(s) of the expression level(s) of the target small RNA(s) in each one of the subsequent sample(s), thereby carrying out correction of the expression level(s) of the target small RNA(s) in each of the subsequent sample(s). In this case, the correction can be expressed as an equation as follows. That is, the corrected expression level Ei of the ith target small RNA in a "sample to be corrected" can be calculated according to Equation 9'.

$$Ei = \log_2 Wi - c_{1-1}' \quad (9')$$

The definition of Wi is the same as in Equation 9 described above.

When the expression level(s) of the target small RNA(s) measured in the second sample is corrected, c2 may be added to, or c2' may be subtracted from, each of the measured values or each of the logarithmic value(s) of the measured values of the expression level(s) of the target small RNA(s) in the second sample. The same applies to the third and following samples. It should be noted that, although the difference between the representative value of the first sample, which is used as the reference sample, and the reference value is, of course, 0, the program(s) may be constituted such that the calculation of adding 0 to, or subtracting 0 from, each of the expression level(s) of the target small RNA(s) in the first sample is carried out.

1-2. Fixed-Value Correction Method

Correction of the expression level(s) of the target small RNA(s) is carried out using each individual correction factor obtained from the difference between the representative value and a fixed value (reference value). That is, when the expression level(s) of the target small RNA(s) in a certain sample is/are corrected, the correction factor for the certain sample ($r_{1-2}$ or $r_{1-2}'$) is used.

When the difference obtained by subtracting the representative value of the amount(s) of the standard substance(s) in each one of the samples from the fixed value is used as the correction factor, that is, when Equation 3 is applied, each individual correction factor is added to the measured value(s) or the logarithmic value(s) of the measured value(s) of the expression level(s) of the target small RNA(s) in each one of the samples, thereby carrying out correction of the expression level(s) of the target small RNA(s) in each of the samples. In this case, the correction can be expressed as an equation as follows. That is, the corrected expression level Ei of the ith target small RNA in a "sample to be corrected" can be calculated according to Equation 10.

$$Ei = \log_2 Wi + r_{1-2} \quad (10)$$

Wi represents the signal measurement value from the area where the ith small RNA-capture probe is immobilized.

In contrast, when the difference obtained by subtracting the fixed value from the representative value of the amount(s) of the standard substance(s) in each sample is used as the correction factor, that is, when Equation 3' is applied, each individual correction factor is subtracted from the measured value(s) or the logarithmic value(s) of the measured value(s) of the expression level(s) of the target small RNA(s) in each one of the samples, thereby carrying out correction of the expression level(s) of the target small RNA(s) in each of the samples. In this case, the correction can be expressed as an equation as follows. That is, the corrected expression level Ei of the ith target small RNA in a "sample to be corrected" can be calculated according to Equation 10'.

$$Ei=\log_2 Wi-r_{1-2}' \tag{10'}$$

The definition of Wi is the same as in Equation 10 described above.

Correction Step-2

The correction step-2 is a process in which correction of the expression level(s) of the target small RNA(s) is carried out using the correction factor obtained in the correction-factor-obtaining step-2, and the correction is carried out by dividing the expression level(s) of the target small RNA(s) by the correction factor or multiplying the expression level(s) by the correction factor. Also in this step, there are two ways of carrying out the correction: one corresponds to the reference sample-obtaining method, and the other corresponds to the fixed-value correction method, in the correction-factor-obtaining step-2.

2-1. Reference Sample-Obtaining Method

Correction of the expression level(s) of the target small RNA(s) in the subsequent sample(s) is carried out using the correction factor obtained for each one of the subsequent sample(s). That is, when the expression level(s) of the target small RNA(s) in the second sample is/are corrected, the correction factor for the second sample ($c2_{2-1}$ or $c2_{2-1}'$) is used and, when the expression level(s) of the target small RNA(s) in the third sample is/are corrected, the correction factor for the third sample ($c3_{2-1}$ or $c3_{2-1}'$) is used.

When the ratio calculated by using the representative value of the standard substance(s) in each one of the subsequent sample(s) to be corrected as a denominator and using the representative value of the amount(s) of the standard substance(s) of the reference sample as a numerator is used as the correction factor, that is, when Equation 5 is applied, the measured value(s) or the logarithmic value(s) of the measured value(s) of the expression level(s) of the target small RNA(s) in each one of the subsequent sample(s) is/are multiplied by each individual correction factor, thereby carrying out correction of the expression level(s) of the target small RNA(s) in each of the subsequent sample(s). In this case, the correction can be expressed as an equation as follows. That is, the corrected expression level Ei of the ith target small RNA in a "sample to be corrected" can be calculated according to Equation 11.

$$Ei=\log_2 Wi \times c_{2-1} \tag{11}$$

Wi represents the signal measurement value from the area where the ith small RNA-capture probe is immobilized.

In contrast, when the ratio calculated by using the representative value of the amount(s) of the standard substance(s) of the reference sample as a denominator and using the representative value of the standard substance(s) in each one of the subsequent sample(s) as a numerator is used as the correction factor, that is, when Equation 5' is applied, the measured value(s) or the logarithmic value(s) of the measured value(s) of the expression level(s) of the target small RNA(s) in each one of the subsequent sample(s) is/are divided by each individual correction factor, thereby carrying out correction of the expression level(s) of the target small RNA(s) in each of the subsequent sample(s). In this case, the correction can be expressed as an equation as follows. That is, the corrected expression level Ei of the ith target small RNA in a "sample to be corrected" can be calculated according to Equation 11'.

$$Ei=\log_2 Wi \div c_{2-1}' \tag{11'}$$

The definition of Wi is the same as in Equation 11 described above.

When the expression level(s) of the target small RNA(s) measured in the second sample is to be corrected, the measured value(s) or the logarithmic value(s) of the measured value(s) of the expression level(s) of the target small RNA(s) in the second sample may be divided by $c2_{2-1}$, or may be multiplied by $c2_{2-1}'$. The same applies to the third and following samples. The finally obtained value of the corrected expression level Ei of the target small RNA is the same between the procedures based on Equations 5 and 11 and the procedures based on Equations 5' and 11'. It should be noted that, although the ratio between the representative value for the first sample used as the reference sample and the reference value is, of course, 1, the program(s) may be constituted such that the calculation of multiplying or dividing each of the expression level(s) of the target small RNA(s) in the first sample by 1 is carried out.

2-2. Fixed-Value Correction Method

Correction of the expression level(s) of the target small RNA(s) is carried out using each individual correction factor obtained from the ratio to a fixed value (reference value). That is, when the expression level(s) of the target small RNA(s) in a certain sample is/are corrected, the correction factor for the certain sample ($r_{2-2}$ or $r_{2-2}'$) is used.

When the ratio calculated by using the representative value of the amount(s) of the standard substance(s) in each of the samples as a denominator and using a fixed value as a numerator is used as the correction factor, that is, when Equation 7 is applied, the measured value(s) or the logarithmic value(s) of the measured value(s) of the expression level(s) of the target small RNA(s) in each one of the samples is/are multiplied by each individual correction factor, thereby carrying out correction of the expression level(s) of the target small RNA(s) in each of the samples. In this case, the correction can be expressed as an equation as follows. That is, the corrected expression level Ei of the ith target small RNA in a "sample to be corrected" can be calculated according to Equation 12.

$$Ei=\log_2 Wi \times r_{2-2} \tag{12}$$

Wi represents the signal measurement value from the area where the ith small RNA-capture probe is immobilized.

In contrast, when the ratio calculated by using the representative value of the amount(s) of the standard substance(s) in each one of the samples as a denominator and using a fixed value as a numerator is used as the correction factor, that is, when Equation 7' is applied, the measured value(s) or the logarithmic value(s) of the measured value(s) of the expression level(s) of the target small RNA(s) in each one of the samples is/are divided by each individual correction factor, thereby carrying out correction of the expression level(s) of the target small RNA(s) in each of the samples. In this case, the correction can be expressed as an equation as follows. That is, the corrected expression level Ei of the ith target small RNA in a "sample to be corrected" can be calculated according to Equation 12'.

$$Ei=\log_2 Wi \div r_{2-2}' \tag{12'}$$

The definition of Wi is the same as in Equation 12 described above.

Comparative Analysis Step

Based on the corrected expression level(s) of the target small RNA(s), the expression level(s) of the target small RNA(s) is/are compared among a plurality of samples. When the correction is carried out by the reference sample-obtaining method, the expression level(s) of the target small RNA(s) in the first sample, which is used as the reference sample, is/are not subjected to the correction. Therefore, for example, a comparison between the first sample and the second sample is carried out by comparing the uncorrected expression level of each target small RNA in the first sample to the corrected expression level of each target small RNA in the second sample. Thus, at least one of the samples to be subjected to the comparison is always a corrected sample. Accordingly, the term "based on the corrected expression level(s) of the target small RNA(s), the expression level(s) of the target small RNA(s) is/are compared among a plurality of body fluid samples" includes modes in which a comparison is made between an uncorrected reference sample and a corrected sample(s).

The comparative analysis step itself can be carried out in the same manner as in conventional methods. For example, a scatter diagram of expression level data called scatter plot may be prepared. For example, when carrying out a comparison among three samples, two scatter plots based on comparative analysis between any one of the three samples and each one of the remaining samples (for example, a scatter plot based on comparative analysis between the first sample and the second sample, and a scatter plot based on comparative analysis between the first sample and the third sample) may be prepared and, if necessary, an additional scatter plot based on comparative analysis between the remaining two samples (in the above-exemplified case, between the second sample and the third sample) may be prepared. Comparative analysis among four or more samples may also be carried out in the same manner. In a comparative analysis among three samples, a three-dimensional scatter plot may also be prepared. Even in the reference sample-obtaining method, a comparison between the reference sample and each one of the remaining two samples is not necessarily required and, for example, a comparison between the second sample and the reference sample and a comparison between the second sample and the third sample may be carried out.

The result of the comparative analysis may also be represented by log fold-change, which may be obtained by calculating, based on the corrected expression level of each target small RNA, the difference in the expression level of each target small RNA between any one of the samples and the remaining sample(s). For example, the difference between the expression level of each target small RNA in the reference sample (when the reference sample-obtaining method is employed) or the corrected expression level of each target small RNA in the first sample (when the fixed-value correction method is employed) and the corrected expression level of each target small RNA in each of the subsequent sample(s) may be calculated. Also in this case, similarly to the above-described cases, the calculation of the difference may be carried out not only between the first sample and the remaining sample(s), but also between any one of the subsequent sample(s) and the remaining sample(s). Further, the corrected expression level of each target small RNA may be used to carry out comparison and evaluation by statistical analysis using the expression levels of the target small RNA(s) in a plurality of samples, such as calculation of the average, standard deviation, standard error, and/or coefficient of variation; intergroup comparison and significance test; and cluster analysis.

The device is a device to correct an expression level(s) of a target small RNA(s) for comparative analysis of the said expression level(s). The device comprises:

memory means that memorizes measured values of the expression level(s) of a target small RNA(s) in, and the amount(s) of a standard substance(s) extracted from, each of the samples, wherein the measured values are obtained by measurement using a nucleic acid sample obtained by adding at least one kind of standard substance that is a nucleic acid having a nucleic acid length of not less than 200 bases to each of a plurality of samples, and then extracting nucleic acid from each of the samples;

representative-value-obtaining means that obtains, for each of the samples, a representative value, preferably a representative value expressed as a logarithmic value, from the measured value(s) of the amount(s) of the standard substance(s) extracted;

correction-factor-obtaining means that obtains, as a correction factor for each sample for correction of the expression level(s) of the target small RNA(s) in the each sample, the difference or the ratio between a reference value arbitrarily set in connection with the amount(s) of the standard substance(s) extracted and the representative value obtained for the each sample by the representative-value-obtaining means; and correction means that corrects the expression level(s) of the target small RNA(s) measured in each sample using each correction factor obtained by the correction-factor-obtaining means.

The reference value may be the representative value of the amount(s) of the standard substance(s) in the first sample (reference sample) arbitrarily selected, and the expression level(s) of the target small RNA(s) measured in the subsequent sample(s) may be corrected. That is, the device may comprise:

memory means that memorizes measured values of the expression level(s) of a target small RNA(s) in, and the amount(s) of a standard substance(s) extracted from, each of the samples, wherein the measured values are obtained by measurement using a nucleic acid sample obtained by adding at least one kind of standard substance that is a nucleic acid having a nucleic acid length of not less than 200 bases to each of a plurality of samples, and then extracting nucleic acid from each of the samples;

representative-value-obtaining means that obtains, for each of the samples, a representative value, preferably a representative value expressed as a logarithmic value, from the measured value(s) of the amount(s) of the standard substance(s) extracted;

correction-factor-obtaining means that obtains, using an arbitrarily-selected first sample as a reference sample and using the representative value of the amount(s) of the standard substance(s) extracted in the reference sample as a reference value, the difference or the ratio between the reference value and the representative value in each one of the remaining subsequent sample(s) as a correction factor for the before-mentioned each one of the subsequent sample(s); and correction means that corrects the expression level(s) of the target small RNA(s) measured in each of the subsequent sample(s) using the correction factor for each of the subsequent sample(s) obtained by the correction-factor-obtaining means.

The reference value may be a fixed value arbitrarily defined in connection with the amount(s) of the standard substance(s) extracted, and correction of the expression level(s) of the target small RNA(s) may be carried out for all samples including the first sample. That is, the device may comprise:

memory means that memorizes measured values of the expression level(s) of a target small RNA(s) in, and the amount(s) of a standard substance(s) extracted from, each of the samples, wherein the measured values are obtained by measurement using a nucleic acid sample obtained by adding at least one kind of standard substance that is a nucleic acid having a nucleic acid length of not less than 200 bases to each of a plurality of samples, and then extracting nucleic acid from each sample;

representative-value-obtaining means that obtains, for each of the samples, a representative value, preferably a representative value expressed as a logarithmic value, from the measured value(s) of the amount(s) of the standard substance(s) extracted;

correction-factor-obtaining means that obtains, using a fixed value as a reference value, the difference or the ratio between the reference value and the representative value in each one of the samples as the correction factor for the before-mentioned each one of the samples; and correction means that corrects the expression level(s) of the target small RNA(s) measured in each sample using the correction factor for each sample obtained by the correction-factor-obtaining means.

A device for comparative analysis of the expression levels of small RNAs having the above-described correction device may further comprise output means that outputs a result(s) of comparison of the expression level(s) of the target small RNA(s) among at least two samples based on the corrected expression level(s) of the target small RNA(s).

Figure 2:
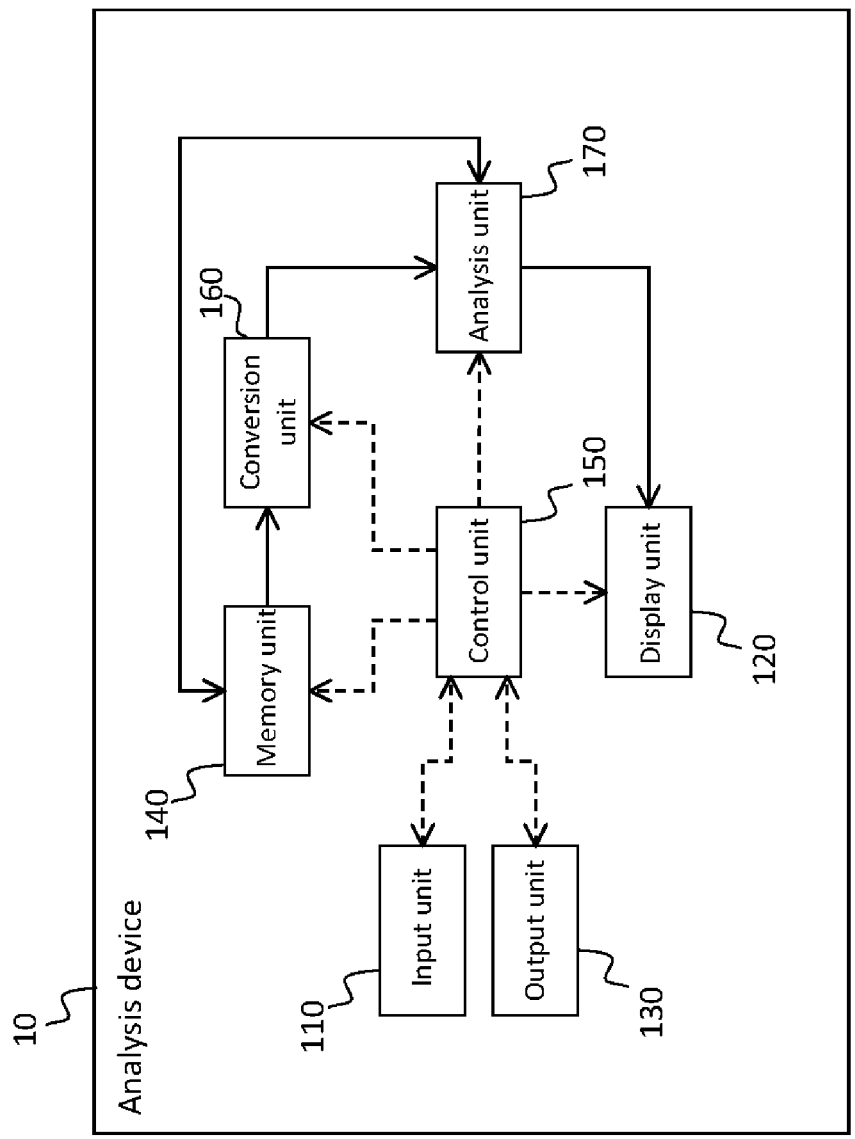
FIG. 2 is a block diagram illustrating an outline of the constitution of the analysis device.
Figure 3:
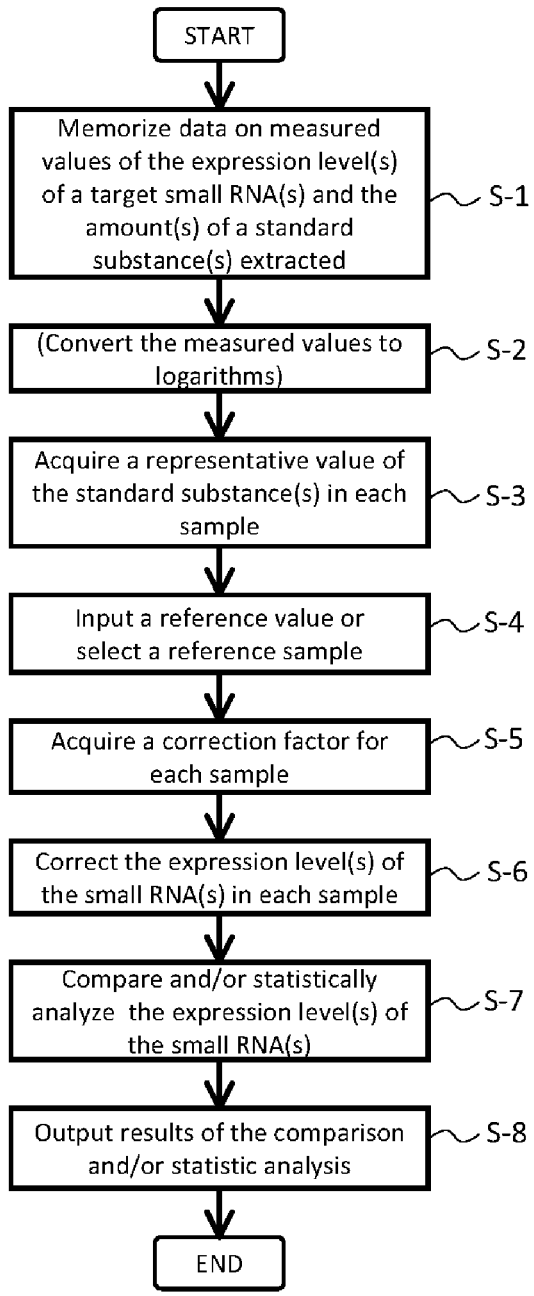
FIG. 3 is an example of the flow chart of the process of correcting the expression levels of target small RNAs.

FIG. 2 shows a block diagram illustrating an outline of the constitution of the analysis device comprising the correction device. An analysis device 10 comprises an input unit 110, display unit 120, output unit 130, memory unit 140, control unit 150, conversion unit 160, and analysis unit 170. FIG. 3 shows an example of the flow chart of the correction process for the expression levels of target small RNAs.

The input unit 110 is a means to input information on the operation by the analysis device 10. Conventionally known input means such as keyboards may be preferably used. When a microarray is used, the data on the expression levels of the small RNAs and the amount(s) of the standard substance(s) extracted obtained by a hybridization assay may be read by reading means such as a scanner separate from the device, and then converted to numerical data. The resulting numerical data may be input from the input unit 110 to the analysis device 10. Or, the reading means such as a scanner may be contained in the analysis device 10 (not shown in the figure).

The data on the expression levels and the extracted amounts input from the input unit 110, or the data on the expression levels and the extracted amounts read and digitized by the reading means incorporated in the analysis device 10, are memorized in the memory unit 140. In this process, the memory unit 140 acts as a memory means that memorizes measured values of the expression levels of a plurality of target small RNAs and a measured value(s) of the amount(s) of at least one standard substance extracted that were simultaneously measured in each one of a plurality of samples.

In some cases, the measured value data on the expression levels of the target small RNAs and the amount(s) of the standard substance(s) extracted in each sample stored in the memory unit 140 are converted to logarithms with base 2 or the like by the conversion unit 160. Subsequently, by the analysis unit 170, a representative value of the measured value(s) of the amount of the standard substance(s) extracted is obtained for each sample. As described in the explanation on the correction method, the representative value may be, for example, the average or the median of the measured value(s) of at least one standard substance (even when only one kind of standard substance is used for the correction, the representative value can be the average or the median when a plurality of probe-immobilized areas for its measurement are present on the array), or may be a measured value of one particular kind of standard substance.

After the representative value is obtained, the difference or the ratio between the reference value and the representative value of the amount(s) of the standard substance(s) in each sample is calculated for each sample by the analysis unit 170 to obtain the correction factor for each sample. Details of process of obtaining the correction factor are as described in the Correction-Factor-Obtaining Step for the correction method. When the reference sample-obtaining method is employed, the program(s) may be constituted such that a correction factor of 0 (when the difference is calculated) or a correction factor of 1 (when the ratio is calculated) is obtained for the first sample, which is selected as the reference sample.

When a reference value is to be input, or a reference sample is to be selected in the device 10, it may be carried out by an operator of the device 10 by arbitrarily specifying one sample from the input unit 110. Or, the device 10 may automatically select the reference value, or select one sample as the reference sample. For example, after the input of data from the input unit 110, a sample whose data are first memorized in the memory unit 140 may be selected as the reference sample by the device 10. In FIG. 3, for convenience, the step of selection of or input of the reference sample is positioned after the representative-value-obtaining step (S-3). However, the position of this step is not limited thereto, and the step may also be carried out as an earlier step, for example, when the data are stored. Or, a preliminarily assigned fixed value may be registered in the conversion unit 160 or the like as the reference value.

Next, the analysis unit 170 corrects the data on the measured expression levels of the target small RNAs using the correction factor for each sample. Details of the correction operation are as described in the Correction Step for the correction method. When the reference sample-obtaining method is employed, the program(s) may be constituted such that the correction operation is carried out for the data on the expression levels of the target small RNAs in the first sample, which is selected as the reference sample, using a correction factor of 0 (when the difference is calculated) or a correction factor of 1 (when the ratio is calculated).

Next, the analysis unit 170 carries out a comparison and/or statistical analysis of the expression levels of the target small RNAs in each sample. The results of the comparison and/or the statistical analysis are output by the output unit 130 to the display unit 120 to be displayed. In addition, the results of the comparison and/or the statistical analysis may be output to an output device such as a printer; recording medium; and/or the like. The output unit 130 can also be constituted such that it outputs the results of the comparative analysis and/or the results of the statistical analysis through a network to an external memory device such as a database present outside the device.

The memory unit 140 memorizes the measured values of the expression levels of a plurality of target small RNAs and the measured values of the amounts of a plurality of standard substances extracted, and also memorizes as appropriate the interim results generated in each of the above-described steps.

The above-described operations by the device 10 are controlled by the control unit 150. More specifically, as indicated by dashed arrows in FIG. 2, control information is output from the control unit 150 to the means, i.e., input unit 110, display unit 120, output unit 130, memory unit 140, control unit 150, conversion unit 160, and analysis unit 170, and these means work in concert in accordance with the control information, to allow the operation of the entire device 10.

We also provide a program(s) that causes a computer(s) to function as the above-described correction device or analysis device. More specifically, the program(s) is/are a program(s) that causes a computer(s) to function as the above-described means (that is, memory means, representative-value-obtaining means, correction-factor-obtaining means, correction means, and moreover, for the analysis device, output means). We also provide a program(s) that causes a computer(s) to execute the steps of the above-described correction method or a comparative analysis method including the correction method. The correction method may comprise the above-described measurement step, representative-value-obtaining step, correction-factor-obtaining step, and correction step, and the comparative analysis method may further comprise a comparative analysis step of comparing the expression level(s) of a target small RNA(s) among a plurality of samples based on the corrected expression level(s) of the target small RNA(s). These programs are programs that cause a computer(s) to execute the correction of the expression level(s) of the target small RNA(s) using data on the measured value(s) of the amount(s) of the standard substance(s) extracted which is/are simultaneously measured with the expression level(s) of the target small RNA(s) using a microarray or the like.

We still further provide a computer-readable recording medium in which any of the program(s) described above is recorded.

The "recording medium" may be an arbitrary "portable physical medium" (non-transient recording medium) such as a flexible disk, magnetic optical disk, ROM, EPROM, EEPROM, CD-ROM, MO, or DVD. Or, the "recording medium" may be a "communication medium" which retains the program(s) for a short period, such as a communication line or a carrier wave used in transmitting the program(s) via a network represented by LAN, WAN, or internet.

The "program" is a data processing method written in an arbitrary language or by an arbitrary description method, and may be in any format including source code and binary code. The "program" is not limited to a single configuration, and includes a program having a distributed configuration as a plurality of modules and/or libraries, and a program which implements its function in cooperation with a separate program(s) represented by an OS (Operating System). In each of the devices shown, a well-known constitution and procedure can be used as a specific constitution to read the recording medium, for a reading procedure, an installation procedure after the reading and the like.

An array chip containing a support on which a plurality of target small RNA-capture probes and at least one, preferably a plurality of, standard substance-capture probes are immobilized, which can be preferably used, can be provided as a chip for small-RNA expression analysis. Preferred conditions for this chip are as described for the measurement step.

EXAMPLES

Our methods, devices, programs, recording media and chips are described below concretely by way of Examples to which the correction method was applied using human serum samples. However, this disclosure is not limited to the following Examples.

Standard Substances

As the standard substances having a nucleic acid length of not less than 200 bases for Examples, the following RNAs were used:

NMIJ CRM 6204-a, which can be purchased as aqueous ribonucleic acid (RNA) solutions for quantitative analysis from National Institute of Advanced Industrial Science and Technology, and is a certified reference material consisting of five kinds of aqueous RNA solutions having the following sample names: RNA500-A (SEQ ID NO:1), RNA500-B (SEQ ID NO:2), and RNA500-C(SEQ ID NO:3) (these RNAs have a nucleic acid length of about 500 bases), and RNA1000-A (SEQ ID NO:4) and RNA1000-B (SEQ ID NO:5) (these RNAs have a nucleic acid length of about 1000 bases); and three kinds of RNAs, hsncs_071028 (SEQ ID NO:15), hsncs_404161 (SEQ ID NO:16), and hsncs_647981 (SEQ ID NO:17) (these RNAs have a nucleic acid length of about 200 bases), which were designed by us and produced by custom synthesis by Eurofins Genomics K. K.

As the standard substances having a nucleic acid length of less than 200 bases for Comparative Examples, cel-miR-39 (SEQ ID NO:6), cel-miR-54 (SEQ ID NO:7), ath-mir-159a (SEQ ID NO:8), and cel-miR-238 (SEQ ID NO:9), which are non-human-derived miRNAs having a nucleic acid length of 20 bases shown in Nobuyoshi Kosaka Edit., "Circulating MicroRNAs: Methods and Protocols (Methods in Molecular Biology)", p 1-p 10, Human Press, New York (2013), were selected. Each miRNA was synthesized by Eurofins Genomics K. K. as an RNA whose 5'-end was modified with a phosphate group. In addition, five kinds of non-biologically derived RNAs having a nucleic acid length of 60 bases commercially available from Eurofins Genomics K. K., H2NC000001 (SEQ ID NO:10), H2NC000002 (SEQ ID NO:11), H2NC000003 (SEQ ID NO:12), H2NC000005 (SEQ ID NO:13), and H2NC000006 (SEQ ID NO:14), were used.

Physical properties and the like of each standard substance are shown in Table 1. All standard substances used were confirmed to have a sequence homology of not more than 50% to any of the human gene transcripts deposited in the public database BLAST.

TABLE 1

| Standard substance | SEQ ID NO: | Base length | GC content (%) | Tm value (° C.) |
|---|---|---|---|---|
| RNA500-A | 1 | 533 | 47 | 89.15 |
| RNA500-B | 2 | 533 | 49 | 89.83 |
| RNA500-C | 3 | 533 | 45 | 88.96 |
| RNA1000-A | 4 | 1033 | 50 | 91.21 |
| RNA1000-B | 5 | 1033 | 49 | 91.12 |
| cel-miR-39 | 6 | 22 | 50 | 65.99 |
| cel-miR-54 | 7 | 24 | 42 | 62.93 |
| ath-mir-159a | 8 | 21 | 43 | 62.61 |
| cel-miR-238 | 9 | 23 | 43 | 64.19 |
| H2NC000001 | 10 | 69 | 52 | 83.56 |
| H2NC000002 | 11 | 69 | 43 | 79.96 |
| H2NC000003 | 12 | 69 | 55 | 85.51 |
| H2NC000005 | 13 | 69 | 46 | 81.42 |
| H2NC000006 | 14 | 69 | 54 | 84.86 |
| hsncs_071028 | 15 | 201 | 51 | 89.95 |
| hsncs_404161 | 16 | 200 | 51 | 89.54 |
| hsncs_647981 | 17 | 204 | 47 | 87.21 |

Design of Capture Probes

As target small RNAs, 2555 kinds of human miRNAs obtained from miRBase Release 19 were selected, and DNAs having their complementary sequences were used as target small RNA-capture probes (Sanger Software, UK).

As the standard nucleic acid substance-capture probes for Examples, DNAs having the sequences complementary to the sequences of the above-described RNA500-A, RNA500-B, RNA500-C, RNA1000-A, RNA1000-B, hsncs_071028, hsncs_404161, and hsncs_647981 were used.

As the standard substance-capture probes for Comparative Examples, DNAs having the complementary sequences of cel-miR-39 (22 bases), cel-miR-54 (24 bases), ath-mir-159a (21 bases), and cel-miR-238 (23 bases) obtained from miRBase were used. In addition, DNAs having the complementary sequences of the above-described five kinds of commercially available RNAs (H2NC000001, H2NC000002, H2NC000003, H2NC000005, and H2NC000006) were used.

As the target small RNA-capture probes and the standard nucleic acid substance-capture probes, synthetic DNAs having an amino group introduced to the 3'-end (produced by custom synthesis by Eurofins Genomics K. K.) were used.

Preparation of DNA Microarray

The 2555 kinds of target small RNA (miRNA)-capture probes and the total of 17 kinds of standard substance-capture probes described above having an amino group introduced to the 3'-end were immobilized on protruded portions of a "3D-GENE" (registered trademark) substrate (substrate having 3000-columnar structure) manufactured by Toray Industries, Inc., to prepare a DNA microarray. Each standard substance-capture probe was immobilized at eight positions. Using this DNA microarray, the following experiments were carried out.

Addition of Standard Substances to Serum Samples and Step of Extraction of Nucleic Acids With 300 μL of each serum sample, 900 μL of 3D-GENE RNA extraction reagent from liquid sample (Toray Industries, Inc.) which is RNA extraction reagent was mixed. In Examples, 10 fmol of at least one of the above-described standard substances for Examples, that is, RNA500-A, RNA500-B, RNA500-C, RNA1000-A, RNA1000-B, hsncs_071028, hsncs_404161, and hsncs_647981, was added. In Comparative Examples, 10 fmol of at least one of the above-described standard substances for Comparative Examples, that is, cel-miR-39, cel-miR-54, ath-mir-159a, cel-miR-238, H2NC000001, H2NC000002, H2NC000003, H2NC000005, and H2NC000006, was added. Each resulting mixture was subjected to centrifugation, and the aqueous layer as the upper layer was collected, followed by purification of RNA using a miRNeasy mini kit (QIAGEN).

Step of Measurement of Expression Levels of Target Small RNAs (miRNAs) and Amounts of Standard Substances Extracted, by DNA Microarray The obtained target small RNAs (miRNAs) were labeled using the 3D-GENE miRNA labeling kit (Toray Industries, Inc.). The labeled miRNAs were subjected to hybridization and washing according to the standard protocol for the 3D-GENE miRNA chip (Toray Industries, Inc.). The DNA microarray after the reaction was subjected to detection of fluorescence signals using a microarray scanner (Toray Industries, Inc.). Settings of the scanner were as follows: laser output, 100%; photomultiplier voltage, 42%.

Example 1

According the procedure described above, the standard substances for Examples shown in SEQ ID Nos:1 to 5 (all of the five kinds of substances) or the standard substances for Examples shown in SEQ ID Nos:15 to 17 (all of the three kinds of substances) were added to 300 μL of a commercially available serum sample, and the step of extraction of nucleic acid and the step of measurement of the expression levels of the target small RNAs (miRNAs) and the amounts of standard substances extracted, by DNA microarray was carried out. The above-described steps were carried out in 10 replicates for comparison of the effect of correcting interexperimental fluctuation (variation) of the measured values of the expression levels among the measurement experiments.

As a result, about 1000 out of the 2555 kinds of miRNAs were detected. The median of all the CV (coefficient of variation) values of the said about 1000 kinds of detected miRNAs among the 10 replicates of measurement experiments for their expression levels was 0.45 before the correction.

The correction of the expression level of each miRNA was carried out as follows. First, the abundance of each standard substance in each experiment was calculated as the average of the measured values from the eight positions on the DNA microarray, and this was used as a representative value. Subsequently, the representative value of the standard substances in the first experiment was provided as a reference value, and the ratios between the representative value and the representative values in the second to tenth experiments were obtained as correction factors. Using these correction factors, correction of the measured values of the expression levels of the miRNAs in the second to tenth experiments was carried out. As a result, after the correction, the median of all the CV values of the said about 1000 kinds of detected miRNAs among the 10 replicates of measurement experiments for their expression levels was 0.32 (SEQ ID NO:1), 0.40 (SEQ ID NO:2), 0.40 (SEQ ID NO:3), 0.38 (SEQ ID NO:4), 0.30 (SEQ ID NO:5), 0.41 (SEQ ID NO:15), 0.36 (SEQ ID NO:16), or 0.39 (SEQ ID NO:17), respectively.

Comparative Example 1

Experiments were carried out in the same manner as in Example 1 except that the nine kinds of standard substances for Comparative Examples shown in SEQ ID Nos:6 to 14 were used instead of the standard substances for Examples shown in SEQ ID Nos:1 to 5.

The median of the CV values of the expression levels of the about 1000 kinds of miRNAs detected was 0.45 before the correction.

After the correction, the median of the CV values of the expression levels of the miRNAs was 1.07 (SEQ ID NO:6), 1.14 (SEQ ID NO:7), 0.98 (SEQ ID NO:8), 0.99 (SEQ ID NO:9), 0.94 (SEQ ID NO:10), 0.95 (SEQ ID NO:11), 0.84 (SEQ ID NO:12), 0.82 (SEQ ID NO:13), or 0.88 (SEQ ID NO:14), respectively.

Thus, the median of the CV values of the detected values of the target small RNAs after the correction in Example 1 was smaller than that before the correction, 0.45, whereas, the median in Comparative Example 1 after the correction was larger than that before the correction, 0.45. That is, it was shown that, in correction of the interexperimental fluctuation (variation) of the expression level among experiments in which the process from the extraction of nucleic acid to the DNA microarray experiment was carried out a plurality of times using the same samples, the accuracy of the correction could be improved by carrying out the cor-

Example 2

Using each of the three kinds of sera A to C collected from three human individuals, and using as standard substances the standard substances for Examples that are shown in SEQ ID Nos:1 to 5, addition of the standard substances to the serum sample, the step of extraction of nucleic acid, and the step of measurement of the expression levels of target small RNAs and the abundances of the standard substances by DNA microarray were carried out twice (the first experiment and the second experiment) for each serum by the above-described procedure under conditions where the date of extraction of nucleic acid and the experimenter were different. As the target small RNAs (miRNAs), the about 1000 kinds of miRNAs detected were used similarly to Example 1.

The correction of the measured value of each miRNA that is a target small RNA was carried out as follows.

First, the abundance of each standard substance obtained in the measurement step was calculated as the average of the measured values from the eight positions on the DNA microarray, and this was converted to a base 2 logarithm. Subsequently, the average of the logarithmically converted values obtained for the five kinds of standard substances was calculated to provide a representative value. As described above, the representative values for the first experiment and the second experiment were calculated for each of the sera A to C. The logarithmically converted values for the standard substances and the average thereof (representative value) are shown in Table 2.

In the correction of the expression level of each miRNA between the two experiments for each of the sera A to C, the representative value for the first experiment was used as the reference value, and the difference between the reference value and the representative value for the second experiment (second experiment−first experiment) was provided as the correction factor for each serum (Table 3).

Subsequently, the measured values of the expression levels of the miRNAs in each serum were converted to base 2 logarithms, and the above-described correction factor for each serum was subtracted from the logarithmically converted values obtained in the second experiment for each serum to carry out correction.

By the above operation, correction of the measured values of the expression levels of the miRNAs in the second experiment was carried out.

Example 3

Experiments were carried out in the same manner as in Example 2 except that the standard substances for Examples that are shown in SEQ ID Nos:15 to 17 were used as standard substances.

Comparative Example 2

Experiments were carried out in the same manner as in Example 2 except that the standard substances for Comparative Examples that are shown in SEQ ID Nos:6 to 9 were used as standard substances.

Comparative Example 3

Experiments were carried out in the same manner as in Example 2 except that the standard substances for Comparative Examples that are shown in SEQ ID Nos:10 to 14 were used as standard substances.

Figure 4B:
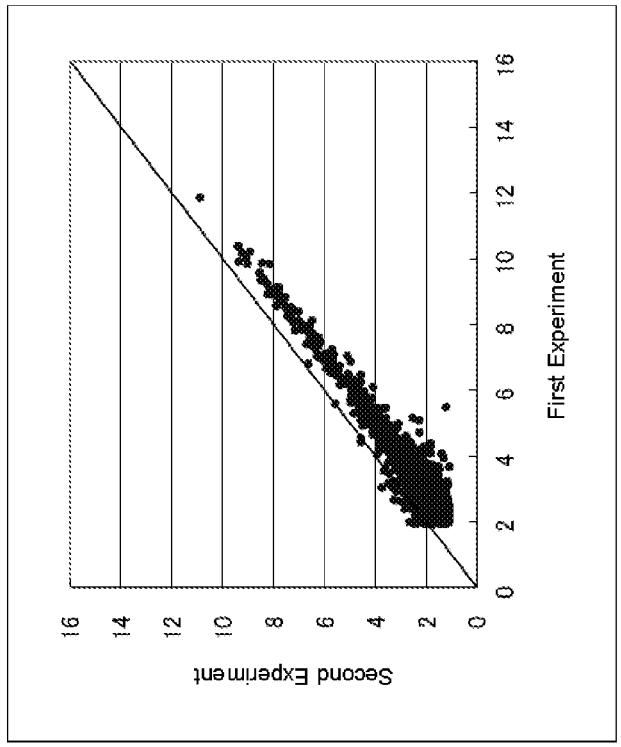
FIGS. 4A and 4B are diagrams showing (FIG. 4A) a scatter plot after carrying out the correction according to Example 2 and (FIG. 4B) a scatter plot after carrying out the correction according to Comparative Example 2.
Figure 4A:
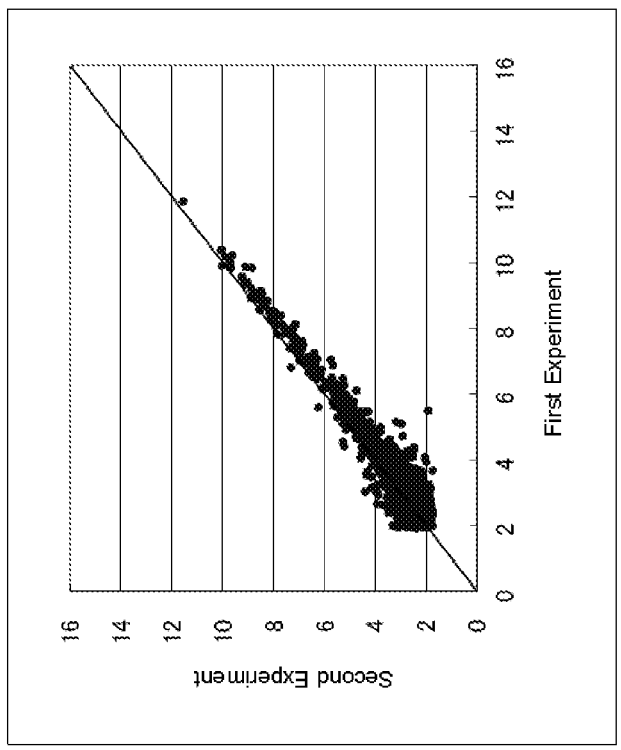

For each of the experiments of Example 2, Example 3, Comparative Example 2, and Comparative Example 3, the results of calculation of the regression line between the measured values of the expression levels of the target small RNAs in the first experiment (reference sample) and the corrected measured values of the expression levels of the miRNAs in the second experiment (sample to be corrected) are shown in Table 4. Scatter plots (serum A) in which the expression levels in the first experiment (reference sample, without correction) and the second experiment (sample to be corrected, with correction) are plotted along the abscissa and the ordinate, respectively, are shown in FIGS. 4A and 4B ((FIG. 4A): results of the correction in Example 2; (FIG. 4B): results of the correction in Comparative Example 2).

Since the same sera were used in the first experiment and the second experiment, the results of these experiments (the results for the samples in the first experiment and the corrected results for the samples in the second experiment) should originally be the same between these experiments, and the regression line should coincide with the y=x line. Examples 2 and 3 and Comparative Examples 2 and 3 showed the same slope. However, while Examples 2 and 3 showed an absolute value of the intercept of <0.5 to give a line almost coincident with the y=x line, Comparative Examples 2 and 3 showed an absolute value of the intercept of >0.5 to give a line largely shifted from the y=x line.

As described above, in Examples 2 and 3, the corrected data obtained gave a regression line that is close to y=x with an absolute value of the intercept of 0 between the two measurement experiments, suggesting high accuracy of the corrected data. On the other hand, in Comparative Examples 2 and 3, the absolute value of the intercept of the regression line was larger than 0.5 and, hence, low accuracy of the corrected data was suggested.

TABLE 2

| Example | | | Logarithmically converted signal value of standard substance (first experiment and second experiment) | | | | | |
|---|---|---|---|---|---|---|---|---|
| Comparative | Standard | SEQ ID | Serum A | | Serum B | | Serum C | |
| Example | substance | NO: | First | Second | First | Second | First | Second |
| Example 2 | RNA500-A | 1 | 6.608 | 6.659 | 6.635 | 6.820 | 7.115 | 6.812 |
| | RNA500-B | 2 | 5.154 | 5.163 | 5.163 | 5.764 | 6.323 | 5.972 |
| | RNA500-C | 3 | 3.490 | 3.521 | 3.690 | 3.456 | 3.954 | 3.630 |
| | RNA1000-A | 4 | 6.943 | 7.009 | 7.139 | 7.188 | 7.285 | 7.140 |
| | RNA1000-B | 5 | 1.673 | 2.069 | 2.139 | 1.822 | 0.914 | 1.905 |
| | Average in Example 2 | | 4.774 | 4.884 | 4.953 | 5.010 | 5.118 | 5.092 |

TABLE 2-continued

| Example Comparative Example | Standard substance | SEQ ID NO: | Logarithmically converted signal value of standard substance (first experiment and second experiment) | | | | | |
|---|---|---|---|---|---|---|---|---|
| | | | Serum A | | Serum B | | Serum C | |
| | | | First | Second | First | Second | First | Second |
| Example 3 | hsncs_071028 | 15 | 7.721 | 7.947 | 7.424 | 7.118 | 7.234 | 7.002 |
| | hsncs_404161 | 16 | 8.686 | 9.162 | 8.305 | 8.122 | 8.094 | 7.854 |
| | hsncs_647981 | 17 | 6.907 | 6.902 | 6.340 | 6.350 | 6.008 | 5.799 |
| | Average in Example 3 | | 7.771 | 8.004 | 7.356 | 7.197 | 7.112 | 6.885 |
| Comparative Example 2 | cel-miR-39 | 6 | 11.952 | 12.799 | 12.966 | 11.860 | 11.728 | 12.799 |
| | cel-miR-54 | 7 | 12.146 | 13.071 | 13.438 | 11.348 | 10.894 | 12.654 |
| | ath-mir-159a | 8 | 12.818 | 13.412 | 13.617 | 12.917 | 12.838 | 13.595 |
| | cel-miR-238 | 9 | 12.884 | 13.652 | 13.910 | 12.525 | 12.416 | 13.539 |
| | Average in Comparative Example 2 | | 12.450 | 13.234 | 13.483 | 12.162 | 11.969 | 13.147 |
| Comparative Example 3 | H2NC000001 | 10 | 10.912 | 9.946 | 11.645 | 10.952 | 11.031 | 12.243 |
| | H2NC000002 | 11 | 10.923 | 10.227 | 11.839 | 10.221 | 11.188 | 12.287 |
| | H2NC000003 | 12 | 11.051 | 10.743 | 10.325 | 9.551 | 11.221 | 12.045 |
| | H2NC000005 | 13 | 11.150 | 10.698 | 11.249 | 10.353 | 11.014 | 11.531 |
| | H2NC000006 | 14 | 10.835 | 10.033 | 12.145 | 10.759 | 10.645 | 12.432 |
| | Average in Comparative Example 3 | | 10.974 | 10.329 | 11.441 | 10.367 | 11.020 | 12.108 |

TABLE 3

| Example Comparative Example | Correction factor (second experiment - first experiment) | | |
|---|---|---|---|
| | Serum A | Serum B | Serum C |
| Example 2 | 0.110 | 0.057 | −0.027 |
| Example 3 | 0.232 | −0.160 | −0.227 |
| Comparative Example 2 | 0.783 | −1.321 | 1.178 |
| Comparative Example 3 | −0.645 | −1.073 | 1.088 |

TABLE 4

| Example Comparative Example | Regression line (slope/intercept) | | |
|---|---|---|---|
| | Serum A | Serum B | Serum C |
| Example 2 | 0.9207/−0.0118 | 0.9355/−0.0414 | 0.9125/0.0624 |
| Example 3 | 0.9207/−0.1328 | 0.9355/0.2506 | 0.9125/0.2624 |
| Comparative Example 2 | 0.9207/−0.6823 | 0.9355/0.9025 | 0.9125/−0.7069 |
| Comparative Example 3 | 0.9207/0.5205 | 0.9355/0.6325 | 0.9125/−0.6833 |

As can be seen from the Examples 1 to 3 and the Comparative Examples 1 to 3, accurate data for comparative analysis of the expression levels of target small RNAs contained in a plurality of samples can be obtained by use of the correction method, and accurate analysis of the expression levels of the target small RNAs is possible therewith.

The invention claimed is:

1. A method of correcting an expression level(s) of a target small RNA(s) for comparative analysis of the expression level(s) in a plurality of samples utilizing a device that corrects the expression level(s) of the target small RNA(s) for comparative analysis of the expression level(s) in the plurality of samples, the device comprising: a memory means that memorizes the measured values of the expression level(s) of the target small RNA(s) in, and the amount(s) of the standard substance(s) extracted from, each of the samples; a representative-value-obtaining means; a correction-factor-obtaining means; and a correction means, the method comprising:

adding at least one kind of standard substance to each of said plurality of samples, said standard substance being a synthetic nucleic acid with a nucleic acid length of not less than 200 bases, and then extracting nucleic acids from each sample to obtain a nucleic acid sample comprising the target small RNA(s) and said at least one kind of standard substance;

measuring the amounts of the target small RNA(s) and the standard substance(s) present in each extracted nucleic acid sample, to obtain measured values of the expression level(s) of the target small RNA(s) in, and the amount(s) of the standard substance(s) extracted from, each of the samples;

obtaining, with the representative-value-obtaining means, for each of the samples, a representative value from the measured value(s) of the amount(s) of the standard substance(s) extracted;

obtaining, with the correction-factor-obtaining means, as a correction factor for each sample for correction of the expression level(s) of the target small RNA(s) in said each sample, the difference or the ratio between a reference value arbitrarily set in connection with the amount(s) of the standard substance(s) extracted and the representative value of the standard substance(s) obtained for said each sample in the representative-value-obtaining step; and correcting, with the correction means, the expression level(s) of the target small RNA(s) measured in each sample using the correction factor obtained for said each sample.

2. The correction method according to claim 1, wherein the nucleic acid length of said standard substance is 200 bases to 1200 bases.

3. The correction method according to claim 2, wherein the at least one kind of standard substance includes at least one selected from standard substances that are synthetic nucleic acids whose base sequences are SEQ ID Nos:1 to 5 and 15 to 17.

4. The correction method according to claim 1, wherein two or more kinds of standard substances are used.

5. The correction method according to claim 1, wherein the sample is a sample derived from a body fluid.

6. The correction method according to claim 1, wherein the target small RNA is miRNA.

7. The correction method according to claim 1, wherein the extraction of the nucleic acid sample in said extraction step is carried out by the phenol-chloroform method.

8. The correction method according to claim 1, wherein said measurement step comprises carrying out hybridization by bringing a nucleic acid sample labeled with a labeling substance into contact with probes to capture a plurality of target small RNAs and a probe(s) to capture at least one standard substance, said probes being immobilized on a support, and obtaining the expression levels of the target small RNAs and the amount(s) of the standard substance(s) extracted, as signal intensity measurement values.

9. The correction method according to claim 1, wherein the representative value obtained in said representative-value-obtaining step is an average or a median expressed as a logarithmic value calculated from the measured value(s) of the amount(s) of the at least one standard substance extracted.

10. The correction method according to claim 1, wherein said reference value is a fixed value arbitrarily defined in connection with the amount(s) of the standard substance(s) extracted, or a representative value of the amount(s) of the standard substance(s) extracted obtained for a first sample arbitrarily selected from said plurality of samples.

11. The method according to claim 1, wherein the correction is carried out in said correction step as follows:

(a) when a value calculated by subtracting said reference value from said representative value is obtained as a correction factor in said correction-factor-obtaining step, the correction factor is subtracted from the measured value(s) of the expression level(s) of the target small RNA(s);

(b) when a value calculated by subtracting said representative value from said reference value is obtained as a correction factor in said correction-factor-obtaining step, the correction factor is added to the measured value(s) of the expression level(s) of the target small RNA(s);

(c) when a value calculated by dividing said representative value by said reference value is obtained as a correction factor in said correction-factor-obtaining step, the measured value(s) of the expression level(s) of the target small RNA(s) is/are divided by the correction factor; or (d) when a value calculated by dividing said reference value by said representative value is obtained as a correction factor in said correction-factor-obtaining step, the measured value(s) of the expression level(s) of the target small RNA(s) is/are multiplied by the correction factor.

* * * * *